US012582363B2

(12) United States Patent
Gregerson et al.

(10) Patent No.: US 12,582,363 B2
(45) Date of Patent: Mar. 24, 2026

(54) MOBILE X-RAY IMAGING SYSTEM

(71) Applicant: Mobius Imaging, LLC, Shirley, MA (US)

(72) Inventors: Eugene A. Gregerson, Bolton, MA (US); Russell Stanton, Lunenberg, MA (US); Paul Sebring, Townsend, MA (US); Michael Connor, Dunstable, MA (US); Robert Powell, Stow, MA (US)

(73) Assignee: Mobius Imaging, LLC, Shirley, MA (US)

( * ) Notice: Subject to any disclaimer, the term of this patent is extended or adjusted under 35 U.S.C. 154(b) by 0 days.

(21) Appl. No.: 18/608,262

(22) Filed: Mar. 18, 2024

(65) Prior Publication Data

US 2024/0341700 A1 Oct. 17, 2024

Related U.S. Application Data

(60) Division of application No. 17/066,030, filed on Oct. 8, 2020, now Pat. No. 11,957,493, which is a (Continued)

(51) Int. Cl.
| | |
|---|---|
| *A61B 6/03* | (2006.01) |
| *A61B 6/00* | (2006.01) |
| A61B 6/46 | (2024.01) |

(52) U.S. Cl.
CPC ............ *A61B 6/035* (2013.01); *A61B 6/4405* (2013.01); *A61B 6/46* (2013.01); *A61B 6/56* (2013.01)

(58) Field of Classification Search
CPC ......... A61B 6/035; A61B 6/4405; A61B 6/46; A61B 6/56; A61B 5/055
See application file for complete search history.

(56) References Cited

U.S. PATENT DOCUMENTS

| | | |
|---|---|---|
| 4,055,148 A | 10/1977 | Brockman et al. |
| 4,355,410 A | 10/1982 | Sullins |

(Continued)

FOREIGN PATENT DOCUMENTS

| | | |
|---|---|---|
| EP | 0395711 B1 | 3/1995 |
| KR | 19960006653 B1 | 5/1996 |

OTHER PUBLICATIONS

Extended European Search Report received from the European Patent Office in European Application No. 14764980.0-1666/2967476 related to PCT/US2014/027914 dated Oct. 11, 2016.

(Continued)

*Primary Examiner* — Sanjay Cattungal
(74) *Attorney, Agent, or Firm* — Howard & Howard Attorneys PLLC

(57) ABSTRACT

An imaging system includes a first portion and a second portion that translates and/or rotates with respect to the first portion. A first locking mechanism may prevent the second portion from translating with respect to the first portion, such as during transport of the system. A second locking mechanism may prevent the second portion from rotating with respect to the first portion, such as during transport and/or during an imaging scan. Further embodiments include a cable management system between the first and second portions, a spherically-shaped surface of a support gimbal and a user interface device for an imaging system.

17 Claims, 36 Drawing Sheets

Related U.S. Application Data continuation of application No. 14/211,822, filed on Mar. 14, 2014, now Pat. No. 10,835,190.

(60) Provisional application No. 61/800,007, filed on Mar. 15, 2013.

(56) References Cited

U.S. PATENT DOCUMENTS

| | | | |
|---|---|---|---|
| 4,578,919 A | 4/1986 | Amadon et al. | |
| 4,651,099 A | 3/1987 | Vinegar et al. | |
| 4,928,283 A | 5/1990 | Gordon | |
| 4,935,949 A | 6/1990 | Fujita et al. | |
| 4,969,167 A | 11/1990 | Zupancic et al. | |
| 4,977,588 A | 12/1990 | Van der Ende | |
| 5,081,662 A | 1/1992 | Warden et al. | |
| 5,097,132 A | 3/1992 | Plummer | |
| 5,146,094 A | 9/1992 | Stark | |
| 5,448,607 A | 9/1995 | McKenna | |
| 5,448,608 A | 9/1995 | Swain et al. | |
| 5,499,415 A | 3/1996 | McKenna | |
| 5,537,453 A | 7/1996 | Williams et al. | |
| 5,595,409 A | 1/1997 | Fier et al. | |
| 5,638,419 A | 6/1997 | Ingwersen | |
| 5,740,222 A | 4/1998 | Fujita et al. | |
| 5,761,269 A | 6/1998 | Sugihara et al. | |
| 5,784,428 A | 7/1998 | Schmidt | |
| RE36,099 E | 2/1999 | Gordon | |
| 5,912,943 A | 6/1999 | Deucher et al. | |
| 5,956,383 A | 9/1999 | Kendall | |
| 5,982,843 A | 11/1999 | Bailey et al. | |
| 6,104,775 A | 8/2000 | Tuy | |
| 6,131,690 A | 10/2000 | Galando et al. | |
| 6,195,578 B1 | 2/2001 | Distler et al. | |
| 6,198,285 B1 | 3/2001 | Kormos et al. | |
| 6,212,251 B1 | 4/2001 | Tomura et al. | |
| 6,286,696 B1 * | 9/2001 | Van Gorp | B66C 13/00 |
| | | | 212/343 |
| 6,322,251 B1 | 11/2001 | Ballhaus et al. | |
| 6,366,796 B1 | 4/2002 | Yanof et al. | |
| 6,426,989 B2 | 7/2002 | Grass et al. | |
| 6,456,684 B1 | 9/2002 | Mun et al. | |
| 6,490,333 B1 | 12/2002 | Hsieh | |
| 6,609,826 B1 | 8/2003 | Fujii et al. | |
| 6,618,613 B1 | 9/2003 | Shukla et al. | |
| 6,909,775 B2 | 6/2005 | Ray et al. | |
| 6,940,941 B2 | 9/2005 | Gregerson et al. | |
| 6,959,068 B1 | 10/2005 | Sommer | |
| 6,963,632 B2 | 11/2005 | Kendall | |
| 6,988,827 B2 | 1/2006 | Mueller | |
| 6,996,204 B2 | 2/2006 | Grass et al. | |
| 7,001,045 B2 | 2/2006 | Gregerson et al. | |
| 7,072,445 B2 | 7/2006 | Kendall | |
| 7,175,347 B2 | 2/2007 | Tybinkowski et al. | |
| 7,215,805 B2 | 5/2007 | Bruder et al. | |
| 7,224,764 B2 | 5/2007 | Sukovic et al. | |
| 7,311,439 B2 | 12/2007 | Muller | |
| 7,338,207 B2 | 3/2008 | Gregerson et al. | |
| 7,388,941 B2 | 6/2008 | Sukovic et al. | |
| 7,394,888 B2 | 7/2008 | Sukovic et al. | |
| 7,397,895 B2 | 7/2008 | Bailey et al. | |
| 7,410,295 B2 | 8/2008 | Distler et al. | |
| 7,438,471 B2 | 10/2008 | Tybinkowski et al. | |
| 7,490,982 B2 | 2/2009 | Gregerson et al. | |
| 7,568,836 B2 | 8/2009 | Bailey et al. | |
| 7,637,660 B2 | 12/2009 | Tybinkowski et al. | |
| 7,963,696 B2 | 6/2011 | Bailey et al. | |
| 8,118,488 B2 | 2/2012 | Gregerson | |
| 8,251,584 B2 | 8/2012 | Tybinkowski et al. | |
| 8,523,433 B2 | 9/2013 | Butzine et al. | |
| 8,705,695 B2 | 4/2014 | Jabri et al. | |
| 8,737,708 B2 | 5/2014 | Hartmann et al. | |
| 8,746,973 B2 | 6/2014 | Gregerson et al. | |
| 8,753,009 B2 | 6/2014 | Gregerson et al. | |
| 8,770,839 B2 | 7/2014 | Gregerson et al. | |
| 8,888,364 B2 | 11/2014 | Bailey et al. | |
| 9,016,941 B2 | 4/2015 | Tybinkowski et al. | |
| 9,398,886 B2 | 7/2016 | Gregerson et al. | |
| 9,757,593 B2 | 9/2017 | Adler et al. | |
| 9,795,022 B2 | 10/2017 | Duhamel | |
| 9,820,704 B2 | 11/2017 | Tybinkowski et al. | |
| 10,178,981 B2 | 1/2019 | Bailey et al. | |
| 10,835,190 B2 | 11/2020 | Gregerson et al. | |
| 2001/0053203 A1 | 12/2001 | Ishii et al. | |
| 2002/0085681 A1 | 7/2002 | Jensen | |
| 2004/0114723 A1 | 6/2004 | Ray et al. | |
| 2004/0170254 A1 | 9/2004 | Gregerson et al. | |
| 2004/0202287 A1 | 10/2004 | Muller | |
| 2004/0228450 A1 | 11/2004 | Mueller | |
| 2005/0117698 A1 | 6/2005 | Lacey et al. | |
| 2005/0135560 A1 | 6/2005 | Dafni et al. | |
| 2005/0184539 A1 | 8/2005 | Milo | |
| 2006/0184376 A1 * | 8/2006 | Graves | G08B 13/2462 |
| | | | 705/28 |
| 2006/0261296 A1 * | 11/2006 | Heath | G03B 42/02 |
| | | | 250/580 |
| 2007/0069137 A1 | 3/2007 | Campbell et al. | |
| 2007/0092068 A1 | 4/2007 | Albert | |
| 2007/0183588 A1 | 8/2007 | Bailey et al. | |
| 2008/0123818 A1 | 5/2008 | Alder et al. | |
| 2008/0123819 A1 | 5/2008 | Jensen et al. | |
| 2008/0170669 A1 | 7/2008 | Jensen et al. | |
| 2008/0181359 A1 * | 7/2008 | Stayman | A61B 6/08 |
| | | | 378/20 |
| 2008/0306369 A1 | 12/2008 | Udupa | |
| 2009/0041181 A1 | 2/2009 | Krug | |
| 2009/0082661 A1 | 3/2009 | Saladin et al. | |
| 2009/0088138 A1 * | 4/2009 | Jung | H04M 1/642 |
| | | | 455/414.1 |
| 2009/0185663 A1 | 7/2009 | Gaines, Jr. | |
| 2009/0236157 A1 | 9/2009 | Akamatsu | |
| 2009/0310835 A1 * | 12/2009 | Kaus | G06T 17/20 |
| | | | 382/128 |
| 2010/0024128 A1 | 2/2010 | Skripps | |
| 2010/0172468 A1 * | 7/2010 | Gregerson | A61B 6/032 |
| | | | 378/208 |
| 2010/0185198 A1 * | 7/2010 | Piferi | A61B 5/702 |
| | | | 606/54 |
| 2010/0193698 A1 | 8/2010 | Hassan | |
| 2011/0028799 A1 * | 2/2011 | Hyde | A61B 5/0022 |
| | | | 600/300 |
| 2011/0124946 A1 | 5/2011 | Rozas et al. | |
| 2011/0222667 A1 | 9/2011 | Gregerson et al. | |
| 2011/0306882 A1 | 12/2011 | Hannon et al. | |
| 2012/0104264 A1 | 5/2012 | Bailey et al. | |
| 2012/0256099 A1 | 10/2012 | Gregerson et al. | |
| 2012/0330087 A1 | 12/2012 | Gregerson | |
| 2014/0171725 A1 * | 6/2014 | Adler | G21F 3/00 |
| | | | 600/1 |
| 2014/0275953 A1 | 9/2014 | Gregerson et al. | |
| 2015/0313510 A1 * | 11/2015 | Razavi | A61B 6/5288 |
| | | | 600/407 |
| 2017/0007334 A1 | 1/2017 | Crawford et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2018/0207794 A1 | 7/2018 | Sebring et al. | |
| 2018/0214098 A1 | 8/2018 | Tybinkowski et al. | |
| 2021/0022691 A1 | 1/2021 | Gregerson et al. | |

OTHER PUBLICATIONS

International Preliminary Report on Patentability (Chapter 1 of the Patent Cooperation Treaty) in International Application No. PCT/US2014/027914 mailed Sep. 24, 2015.

International Preliminary Report on Patentability issued in PCT Application No. PCT/US2011/024585 mailed Sep. 27, 2012.

International Search Report and Written Opinion issued in PCT Application No. PCT/US2011/024585 mailed Apr. 4, 2011.

International Search Report and Wtitten Opinion of the International Searching Authority issued in PCT Application No. PCT/US2014/027914 mailed Sep. 26, 2014.

(56)     References Cited

OTHER PUBLICATIONS

JUPITER System Brochure from TRUMPF Medezin Systeme Gmbh
& Co. KG of Puccheim, Germany, pp. 1-34, (Nov. 2008).
Supplemental European Search Report received from the European
Patent Office in European Application No. 14764980.0-1666/
2967476 related to PCT/US2014/027914 dated Oct. 28, 2016.

* cited by examiner

SECTION A-A

Battery Charger
Mounted on Gimbal

DOCK DISENGAGED

DOCK ENGAGED

GIMBAL COMPONENT
MOUNTED ON BEARING RETAINING RING

ENLARGED VIEW

MOBILE X-RAY IMAGING SYSTEM

CROSS-REFERENCE TO RELATED APPLICATIONS

This application is a Division of U.S. patent application Ser. No. 17/066,030, filed on Oct. 8, 2020, which is a Continuation of U.S. patent application Ser. No. 14/211,822, filed on Mar. 14, 2014, issued as U.S. Pat. No. 10,835,190, which claims priority to and the benefit of U.S. Provisional Patent Application No. 61/800,007, filed Mar. 15, 2013, the disclosures of each of which are hereby incorporated by reference in their entirety.

BACKGROUND

Conventional medical imaging devices, such as computed tomography (CT) and magnetic resonance (MR) imaging devices, are typically fixed, immobile devices located in a discrete area reserved for imaging that is often far removed from the point-of-care where the devices could be most useful.

It would be desirable to make these imaging devices mobile, so that they can move to various locations within a hospital or other health services environment. This is difficult due to the size, weight and overall number of components required for making an operable imaging system. Furthermore, these systems typically require a power system that can provide high-voltages (e.g., 120 kV) to components that rotate within the system around an imaging bore. Conventional imaging systems generally utilize a dedicated high-voltage power source and a complex power delivery mechanism, such as a slip-ring or a high-voltage cable system, to deliver the required power to the rotating imaging components. While these power systems may work fine for conventional fixed imaging systems, they are not ideal for mobile systems, which are ideally much more compact and lightweight than conventional systems. Furthermore, when transporting a mobile system outside of the traditional radiology environments, it is typically not possible to obtain the power required to perform imaging procedures from standard power outlets.

SUMMARY

Embodiments include an imaging system that includes a first portion comprising a base having a length dimension, a second portion that rotates with respect to the first portion and translates relative to the first portion along the length dimension of the base, and a locking mechanism that prevents the first portion from translating relative to the second portion when the second portion is rotated to a first angular position relative to the first portion and the first portion is at a first translation position along the length dimension.

Further embodiments include an imaging system that includes a first portion of the system, a second portion of the system, wherein the second portion rotates with respect to the first portion, and a locking mechanism having a first lock portion on the first portion of the system and a second lock portion on the second portion of the system, and wherein the first lock portion engages with the second lock portion to prevent the second portion of the system from rotating with respect to the first portion of the system when the second portion of the system is rotated to one or more pre-determined angles relative to the first portion of the system.

Further embodiments include a system that includes a first portion of the system, a second portion of the system having a housing, wherein the second portion of the system rotates with respect to the first portion of the system, and at least one cable that provides an electrical connection between the first and second portions of the system, wherein the at least one cable is fixed at a first position on the first portion of the system and is fixed at a second position on the second portion of the cable, and the rotation of the second portion of the system relative to the first portion of the system in a first direction causes the at one cable to be fed into a service loop located in the housing of the second portion of the system, and the rotation of the second portion of the system relative to the first portion of the system in a second direction opposite the first direction causes the at least one cable to be fed out of the service loop in the housing of the second portion of the system.

Further embodiments include an imaging system that includes a gantry having at least one imaging component, and a gimbal that supports the gantry such that the gantry may tilt with respect to the gimbal in tilt direction, wherein the gimbal has an outer surface facing the gantry that is convexly curved or angled in the gantry tilt direction.

Further embodiments include a control system and a related method for controlling an imaging device, wherein the control system includes a holster mounted to the imaging device, a user interface device removably mounted in the holster and operably connected to a control unit of the imaging device, the user interface device comprising a display configured to display system information and at least one user input component for controlling operation of the imaging device.

Further embodiments include a method of operating an imaging system that includes translating a second portion of the imaging system relative to a first portion of the imaging system, rotating the second portion to a first angular position with respect to the second portion, and engaging a locking mechanism to prevent the first portion from translating relative to the second portion when the second portion is in the first angular position.

Further embodiments include a method of operating an imaging system that includes rotating a second portion of the imaging system with respect to a first portion of the imaging system, and engaging a locking mechanism that prevents the second portion from rotating with respect to the first portion by rotating the second portion to a pre-determined angular position relative to the first portion.

Further embodiments include a method of operating a system having a second portion that rotates with respect to a first portion and at least one cable that provides an electrical connection between the first and second portions of the system, the method including rotating the second portion of the system in a first direction relative to the first portion to feed the at least one cable into a service loop located in a housing of the second portion, and rotating the second portion of the system in a second direction, opposite the first direction, relative to the first portion to feed the at least one cable out of the service loop in the housing of the second portion of the system.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

This application is related to U.S. application Ser. No. 12/576,681, filed Oct. 9, 2009, now U.S. Pat. No. 8,118,488, U.S. application Ser. No. 13/025,566, filed Feb. 11, 2011, and U.S. application Ser. No. 13/025,573, filed Feb. 11, 2011. The entire contents of all of these applications are hereby incorporated by reference for all purposes.

Figure 1:
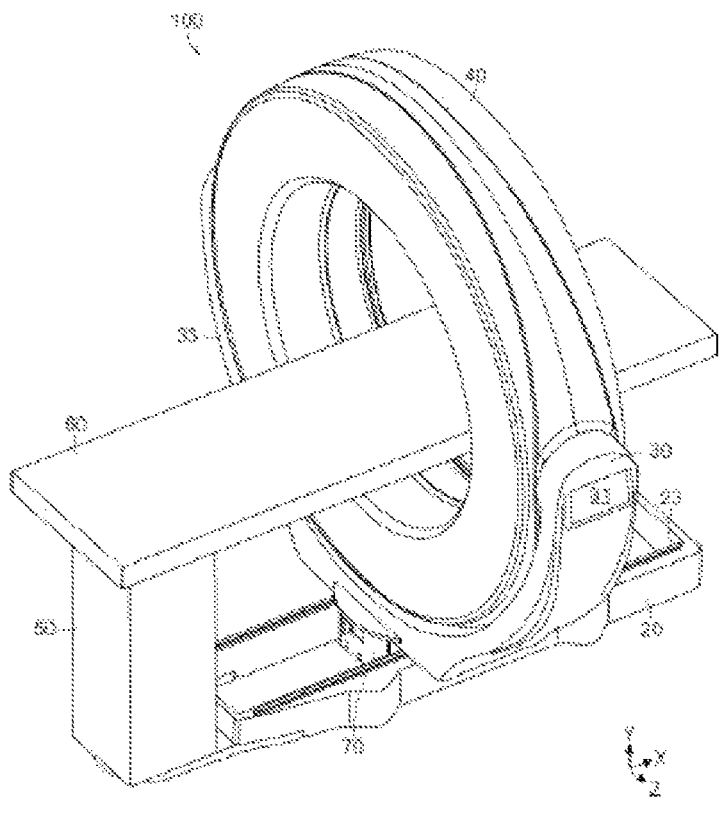
FIG. 1 is a perspective view of an X-ray CT imaging system in accordance with one embodiment of the invention.

Referring to FIG. 1, a mobile imaging system 100 according to one embodiment of the invention includes a mobile base 20, a gimbal 30, a gantry 40, and a pedestal 50. The system 100 includes image collection components, such as a rotatable x-ray source and detector array or stationary magnetic resonance imaging components, that are housed within the gantry 40. The system 100 is configured to collect imaging data, such as, for example x-ray computed tomography (CT) or magnetic resonance imaging (MRI) data, from an object located within the bore of the gantry 40, in any manner known in the medical imaging field. The pedestal 50 is adapted to support a tabletop support 60 that can be attached to the pedestal 50 in a cantilevered manner and extend out into the bore of the gantry 40 to support a patient or other object being imaged.

Figure 2A:
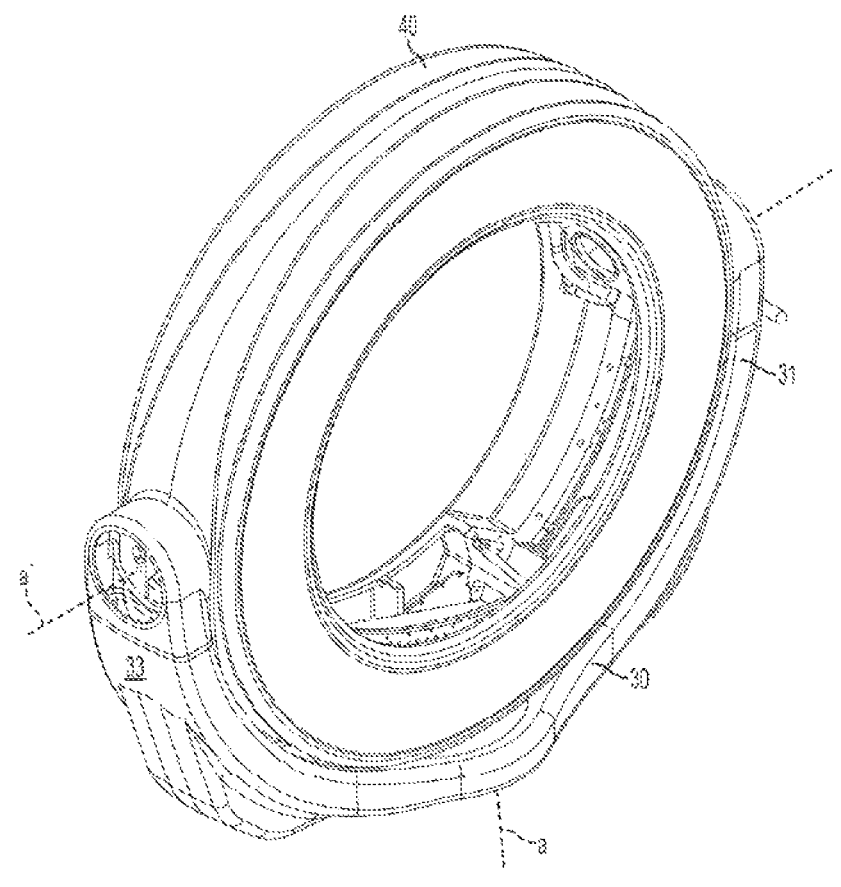
FIG. 2A is a perspective view of a gantry and gimbal.

The gantry 40 and gimbal 30 are illustrated in FIG. 2A. The gimbal 30 is a generally C-shaped support that is mounted to the top surface of base 20 and includes a pair of arms 31, 33 extending up from the base. The arms 31, 33 are connected to opposite sides of gantry 40 so that the gantry is suspended above base 20 and gimbal 30. In one embodiment, the gimbal 30 and gantry 40 can rotate together about a first axis (a) relative to the base 20, and the gantry 40 can tilt about a second axis (a') relative to the gimbal 30 and base 20.

In certain embodiments, the gimbal 30 and gantry 40 can translate with respect to the base 20 to provide an imaging scan. The gimbal 30 can include bearing surfaces that travel on rails 23, as shown in FIG. 1, to provide the translation motion of the gimbal 30 and gantry 20. A scan drive mechanism can drive the translation of the gantry and gimbal relative to the base, and a main drive mechanism can drive the entire system in a transport mode. In the embodiment of FIG. 1, both of these functions are combined in a drive system 70 that is located beneath the gimbal 30.

In certain embodiments, the base 20 of the system can be omitted, and the gimbal 30 can sit directly on the ground to support the gantry 40. In other embodiments, the gimbal can be omitted, and the gantry 40 is a stand-alone gantry that sits on the ground.

Figure 2B:
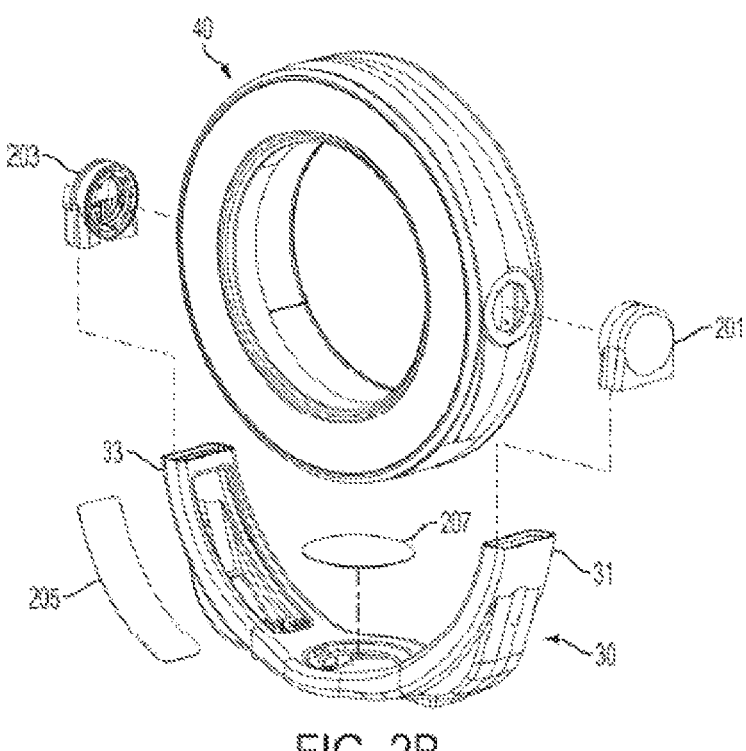
FIG. 2B schematically illustrates the assembly of the gimbal and gantry.
Figure 2C:
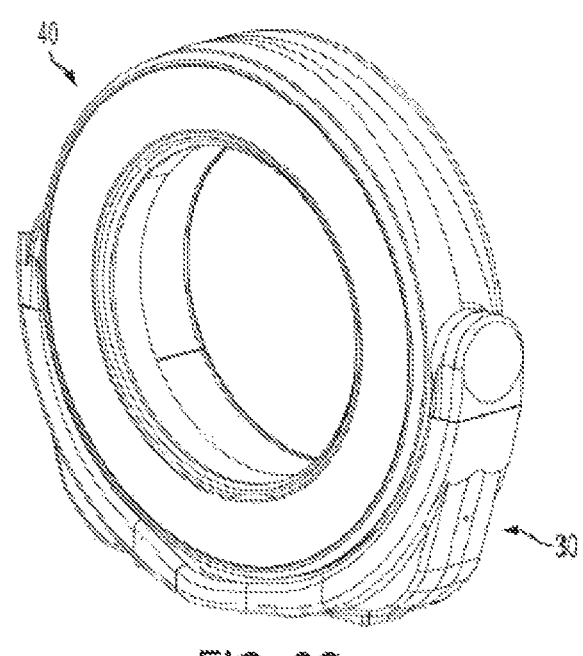
FIG. 2C shows the gimbal and gantry of FIG. 2B fully assembled.

FIG. 2B is an exploded view of the gimbal 30, illustrating how the gimbal 30 may be connected to the gantry 40 in various embodiments. As shown in FIG. 2B, the gimbal 30 may be assembled from multiple pieces. Upper portions 201, 203 of the gimbal 30 may be securely fastened to opposing sides of the gantry 40. The upper portions 201, 203, which may have a shape similar to "earmuffs," may include a bearing apparatus that enables the "tilt" motion of the gantry 40 relative to the gimbal 30. The upper portions 201, 203 may also be fastened to the respective arms 31, 33 of the gimbal 30. For ease of assembly, it may be preferable to fasten the upper portions 201, 203 to the gantry 40 before connecting the entire gantry/upper portion assembly to the respective arms 31, 33 of the gimbal 30. Also shown in FIG. 2B is a cover 205 that may be placed over an access opening in one or both arms 31, 33 of the gimbal 30. An additional cover 207 may be provided over the base of the gimbal 30, and may be removed to access a bearing and/or drive system positioned within or beneath the base of the gimbal 30. The access opening(s) of the gimbal 30 may be sealed by gasket(s) to isolate the interior of the gimbal 30 from the outside environment and facilitate airflow cooling of the system, such as described in U.S. Ser. No. 13/025,573, filed Feb. 11, 2011 and is incorporated by reference herein.

Figure 3A:
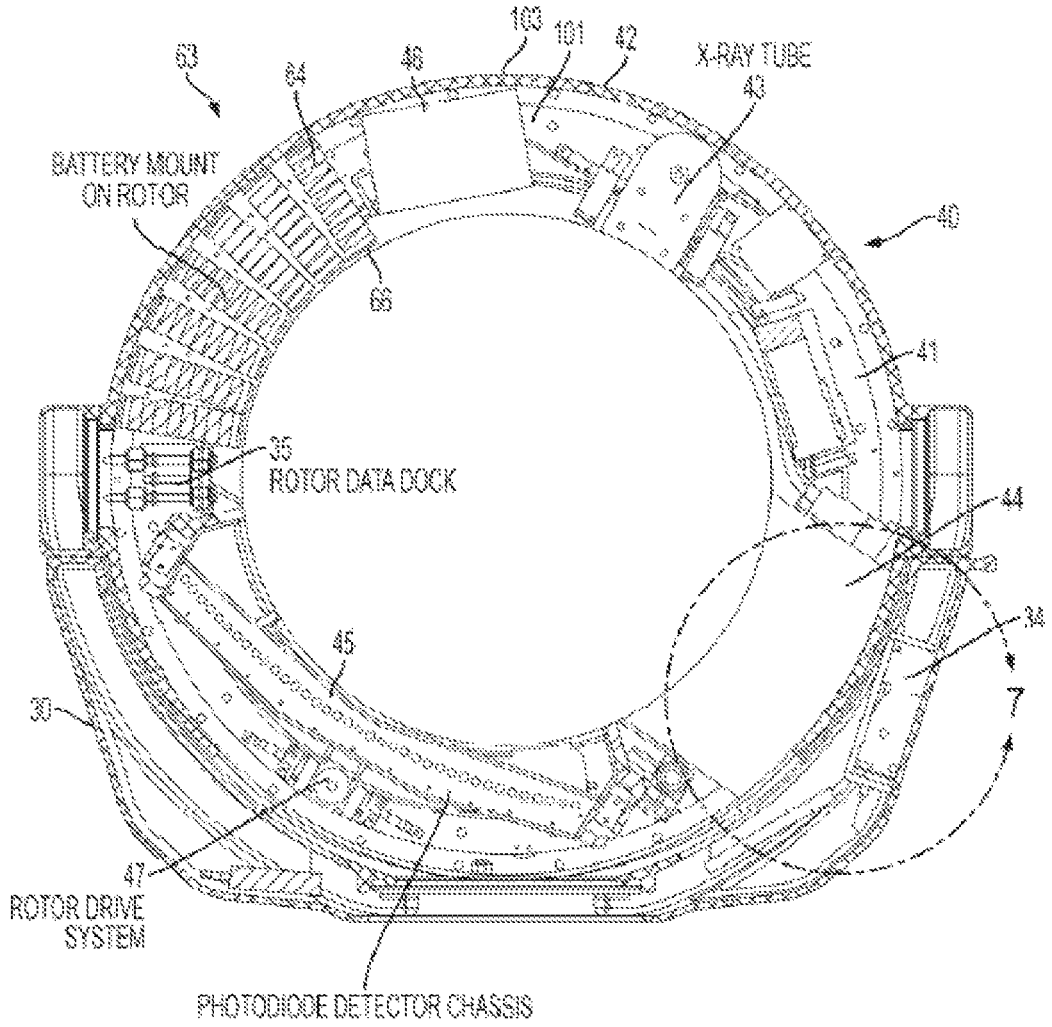
FIG. 3A is a cross-sectional schematic illustration of an imaging system that illustrates the rotating and non-rotating portions of the system.

FIG. 3A is a cross-sectional view of the gantry 40 and gimbal 30 that illustrates a number of components of the imaging system 100, which in this embodiment comprises an X-ray CT imaging system, including an x-ray source 43, high-voltage generator 44, x-ray detector 45, battery system 63, computer 46, rotor drive mechanism 47, docking system 35 and charging system 34. A number of these components, including the x-ray source 43, high-voltage generator 44, x-ray detector 45, battery system 63, computer 46 and rotor drive mechanism 47, are mounted on a rotor 41, as is illustrated in the exploded view of FIG. 3B. The rotor 41 and the components mounted thereto, rotate within a housing defined by an outer shell 42 of the gantry 40.

The system 100 thus has a rotating portion 101, which includes the rotor 41 and the various components mounted to the rotor that rotate within the gantry 40 during an imaging scan, and a non-rotating portion 103, that generally includes the other components of the system, including the base 20, gimbal 30, and the outer shell 42 of the gantry 40. The charging system 34 is located on the non-rotating portion 103 of the system. The docking system 35 provides intermittent connection between the rotating and non-rotating portions 101, 103 for transfer of power and/or data between the two portions.

During an imaging scan, the rotor 41 rotates within the interior of the gantry, while the imaging components such as the x-ray source 43 and x-ray detector 45 obtain imaging data for an object positioned within the bore of the gantry, as is known, for example, in conventional X-ray CT scanners. The rotor drive mechanism 47 drives the rotation of the rotor 41 around the interior of the gantry 40. The rotor drive mechanism 47 may be controlled by a system controller that controls the rotation and precise angular position of the rotor 41 with respect to the gantry 40, preferably using position feedback data, such as from a position encoder device.

Various embodiments of the imaging system 100 may be relatively compact, which may be desirable, for example, in a mobile imaging system. One way in which the system 100 may be made compact is in the design of the gantry 40 and its interface with the rotating portion 101 (e.g., the rotor 41 and the various components mounted to the rotor 41). In embodiments, the outer shell 42 of the gantry 40 may comprise both a protective outer covering for the rotating portion 101 and a mounting surface for a bearing that enables the rotating portion 101 to rotate 360° within the outer shell 42 of the gantry 40.

Figures 4A, 4B:
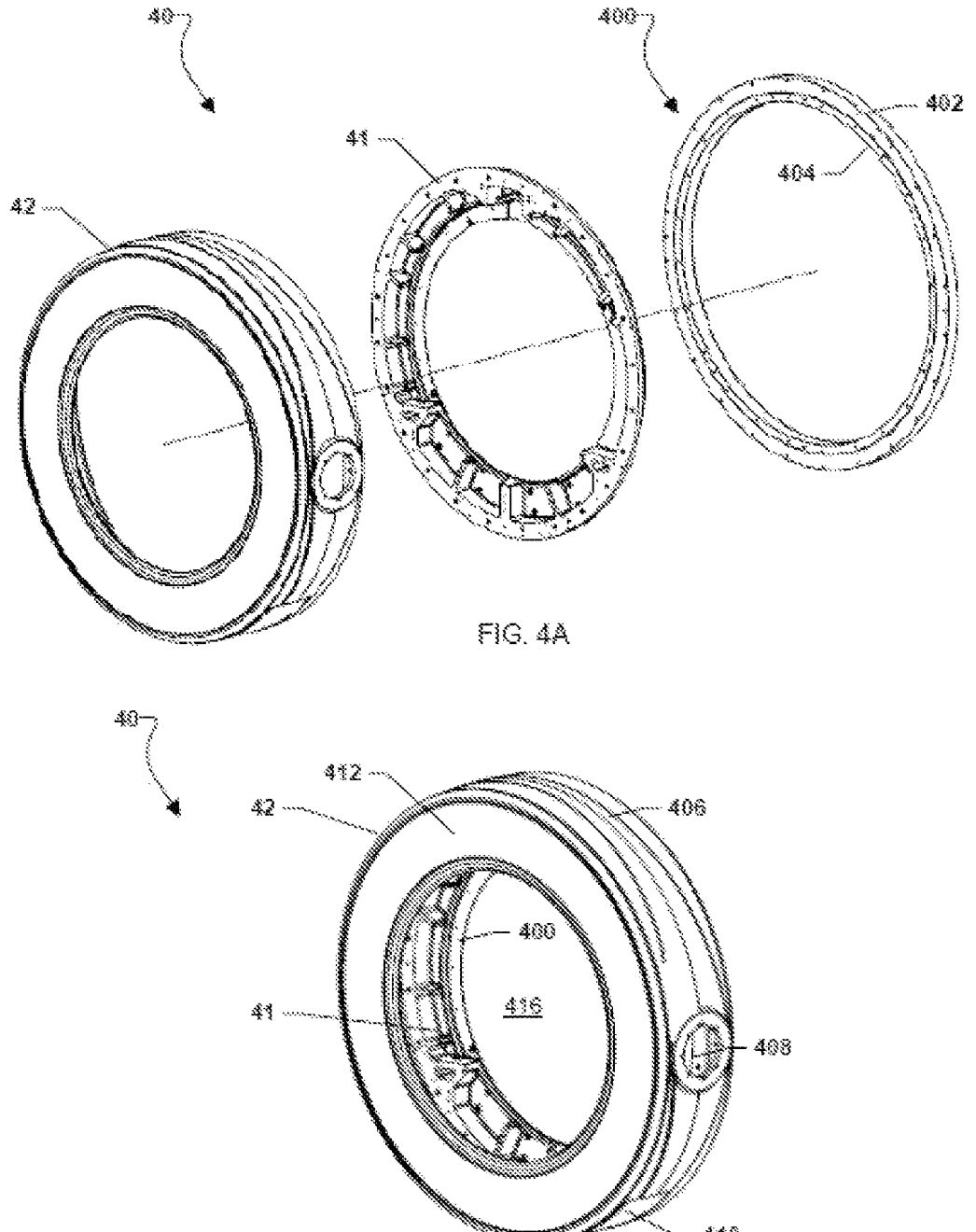
FIG. 4A is an exploded view of a gantry illustrating an outer shell, a rotor and a bearing system according to one embodiment.
FIG. 4B is a perspective view of the assembled gantry.

FIG. 4A is an exploded view of a gantry 40 according to one embodiment that illustrates the outer shell 42, the rotor 41 and a bearing assembly 400. FIG. 4B illustrates the assembled gantry 40. As is shown in FIGS. 4A-B, the outer shell 42 of the gantry 40 may be a generally O-shaped covering of a structural material that may at least substantially fully enclose the rotating portion 101, including the rotor 41 and any components mounted to the rotor, over one or more sides of the rotating portion 101. The outer shell 42 of the gantry 40 may be conceptually considered an "exoskeleton," that both supports the rotating portion 101 of the system 100, preferably in three dimensions, and also provides a protective barrier between the rotating portion 101 and the external environment. In embodiments, the outer shell 42 of the gantry 40 may support at least about 75%, such as more than 80%, and preferably more than about 90%, such as more than 99%, and even more preferably 100% of the weight of the rotating portion 101 of the imaging system 100. In embodiments, the outer shell 42 itself may be supported by one or more other components, such as a gimbal 30, base 20 and/or drive mechanism 70, as shown in FIG. 1, for example. In other embodiments, the outer shell 42 may be supported directly on the ground, for example, or via other means, such as raised on a pedestal, table, cart or other support, or suspended or cantilevered from a wall, ceiling or other support structure. In certain embodiments, an outer shell 42 of the gantry 40 that comprises both a protective outer covering for the rotating portion 101 and a mounting surface for a bearing for rotation of the rotating portion 101 may provide the gantry 40 with various degrees-of-freedom, such as the "tilt" motion about axis (a') and/or rotation about axis (a) as shown in FIG. 2A, as well as translation motion for imaging applications and/or transport of the gantry 40.

The outer shell 42 may be fabricated from a sufficiently rigid and strong structural material, which may include, for example, metal, composite material, high-strength plastic, carbon fiber and combinations of such materials. In preferred embodiments, the outer shell 42 may be comprised of a metal, such as aluminum. The outer shell 42 may be machined or otherwise fabricated to relatively tight tolerances. The outer shell 42 may be formed as a one piece, unitary component. In other embodiments, the outer shell 42 may be comprised of multiple components and/or materials that may be joined using any suitable technique to provide the shell 42.

The outer shell 42 may have an outer circumferential surface 406 that may extend around the periphery of the rotating portion 101 of the system 100 to substantially fully enclose the rotating portion 101 around its outer circumference. As used herein, "substantially fully enclose" means that the circumferential surface 406 encloses at least about 60%, such as at least about 70% (e.g., 75% or more), and preferably at least about 80%, such as at least about 90% (e.g., between 95% and 100%) of the rotating portion 101 around its outer circumference. As shown in FIG. 4B, for example, the outer shell 42 may substantially fully enclose the rotating portion while also including one or more openings, such as opening 408 (where the gantry 40 is secured to the gimbal 30) and access opening 410.

Figures 4C, 4D, 4E:
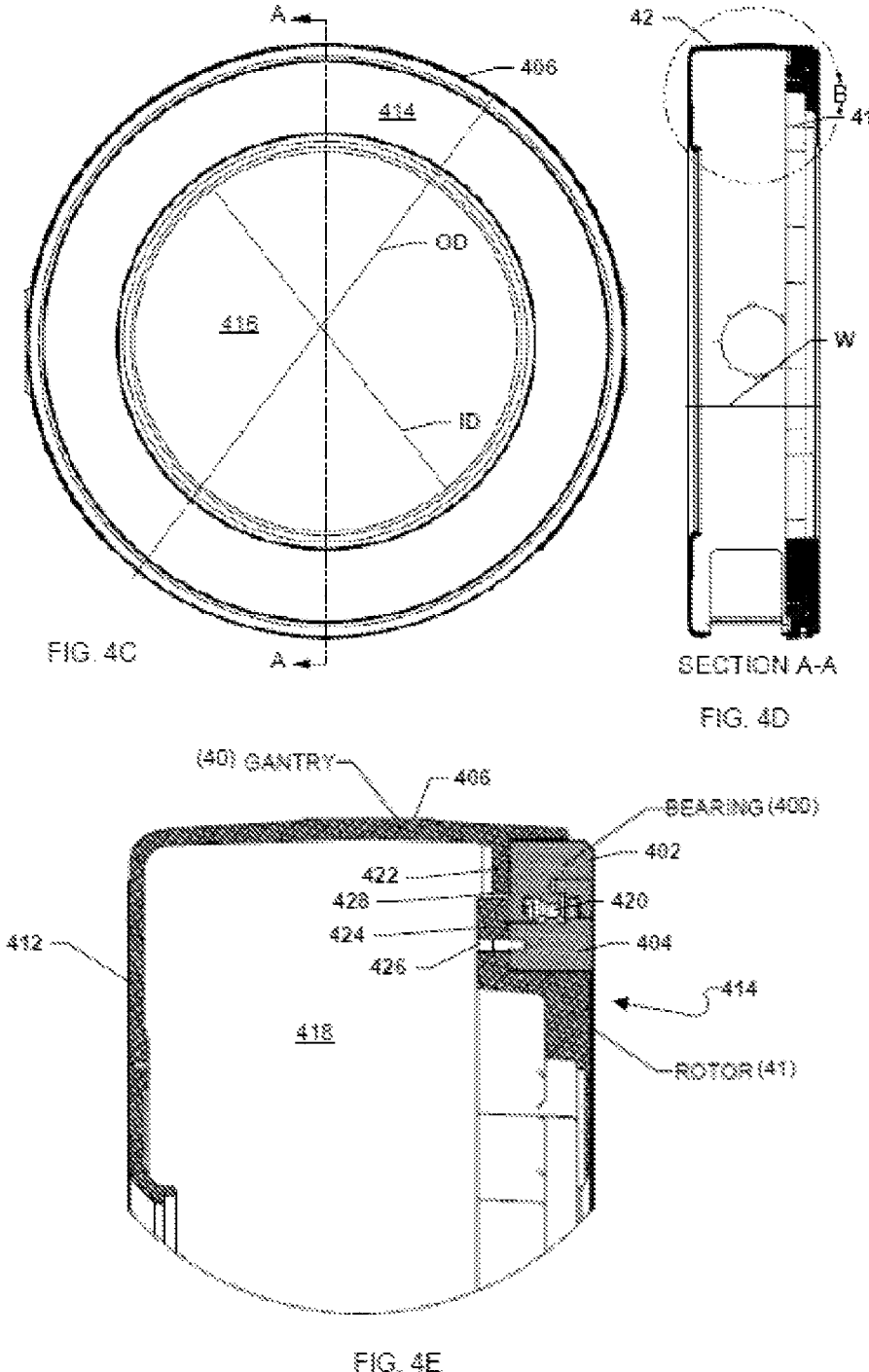
FIG. 4C is a front elevation view of the gantry.
FIG. 4D is a side cross section view of the gantry.
FIG. 4E is a cross-section view of a portion of the gantry illustrating a bearing system in one embodiment.

The outer shell 42 may also include at least one side wall 412 that may extend from the outer circumferential surface 406 to a bore 416 of the gantry 40 and may substantially fully enclose the rotating portion 101 around one side of the rotating portion. In embodiments, the outer shell 42 may include two side walls, one on each side (e.g., front and rear) of the gantry 40, and the two side walls may substantially fully enclose the rotating portion 101 around two sides of the rotating portion. In the embodiment shown in FIGS. 4A-F the outer shell 42 includes a side wall 412 on a first side (e.g., the front side) of the gantry 40. As shown in FIGS. 4C-E, an opposite (e.g., rear) side wall 414 of the gantry 40 may be formed by the combination of the outer shell 42, bearing assembly 400, and/or the rear surface of the rotor 41. The side wall 414 may substantially fully enclose the various components mounted to the rotor 41 around a side of these components. The outer circumferential wall 406 and the side walls 412 and 414 may define a cavity 418, as shown in FIG. 4E, and the various components mounted to the rotor 41 may rotate within the cavity 418. A protective outer covering may be provided over the rear side wall 414 and/or over the interior circumference of the gantry 40 (e.g., around the outer circumference of the bore 416) to provide an additional barrier between the rotating portion 101 and the external environment. The protective covering may be comprised of a thin, lightweight material, such as plastic.

Figure 4F:
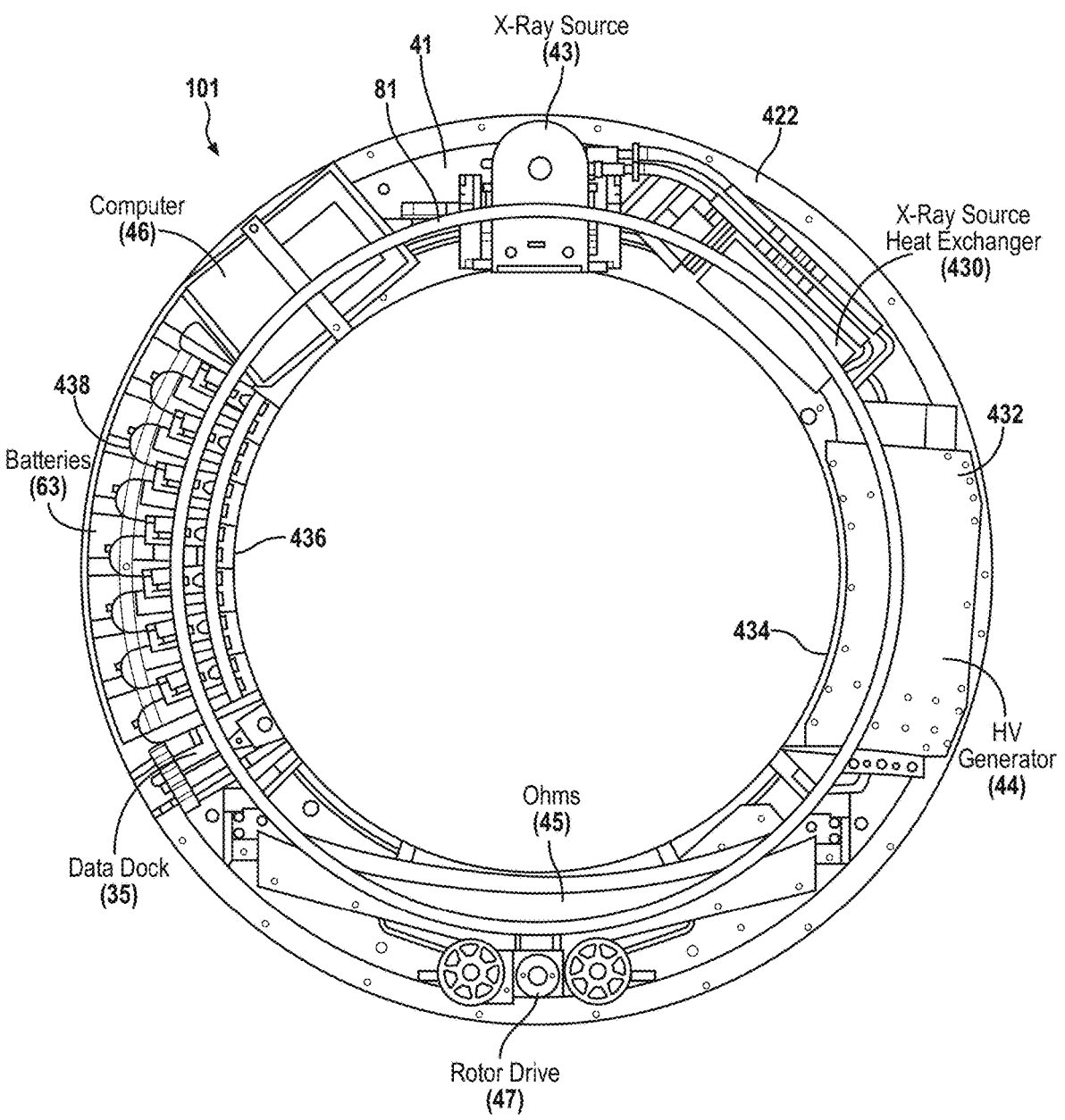
FIG. 4F illustrates an arrangement of components on a rotor according to one embodiment.

As will be discussed in further detail below, the drive mechanism for the rotating portion 101 of the imaging system may utilize a belt drive on the rotor 41, where the belt for the drive is mounted to a fixed railing 81, as is shown in FIG. 4F. In various embodiments, a railing 81 or similar fixed structure for the rotor drive 41 may be located on the internal surface of side wall 412.

The bearing assembly 400 according to one embodiment is shown in FIGS. 4A and 4E. In this embodiment, the bearing assembly 400 includes a first race 402 that may be securely fastened to the outer shell 42 of the gantry 40, and a second race 404 that may be securely fastened to the rotor 41. A bearing element 406 (FIG. 4E) is provided between the first race 402 and the second race 404, and is configured to allow the second race 404 (along with the rotor 41 to which it is attached) to rotate concentrically within the first race 402, preferably with minimal friction, thereby enabling the rotor 41 to rotate with respect to the outer shell 42 of the gantry 40. In the exemplary embodiment of FIG. 4E, the bearing assembly 400 may abut against a lip 424 in the rotor, and a plurality of fastening members 426 (such as bolts) may be provided through the lip 424 and into the second race 404 around the periphery of the rotor 41 to securely fasten the rotor 41 to the bearing assembly 400. The bearing assembly 400 may also be provided at least partially within the outer circumferential wall 406 of the outer shell 42 and against a lip 422 in the outer shell 42 of the gantry 40. A plurality of fastening members (similar to fastening members 426) may be provided through the lip 422 and into the first race 402 around the periphery of the outer shell 42 to securely fasten the outer shell 42 to the bearing assembly 400. A small gap 428 may be provided between lip 422 and lip 424. In some embodiments, all or a portion of the bearing assembly 400 may be integrally formed as a part of the outer shell 42 or of the rotor 41, or of both. For example, the first race 402 may be formed as an integral surface of the outer shell 42 and/or the second race 404 may be formed as an integral surface of the rotor 41. In various embodiments, the entire bearing assembly for enabling the rotation of the rotating portion 101 with respect to the non-rotating portion 103 of the imaging system 100 may be located within the generally O-shaped gantry 40.

The outer diameter of the gantry 40 can be relatively small, which may facilitate the portability of the system 100. In a preferred embodiment, the outer diameter (OD in FIG. 4C) of the gantry 40 is less than about 70 inches, such as between about 60 and 68 inches, and in one embodiment is about 66 inches. The outer circumferential wall 406 of the outer shell 42 may be relatively thin to minimize the OD dimension of the gantry 40. In addition, the interior diameter of the gantry 40, or equivalently the bore 416 diameter (ID in FIG. 4C), can be sufficiently large to allow for the widest variety of imaging applications, including enabling different patient support tables to fit inside the bore, and to maximize access to a subject located inside the bore. In one embodiment, the bore diameter of the gantry 40 is greater than about 38 inches, such as between about 38 and 44 inches, and in some embodiments can be between about 40 and 50 inches. In one exemplary embodiment, the bore has a diameter of about 42 inches. As shown in FIG. 4D, the gantry 40 generally has a narrow profile, which may facilitate portability of the system 100. In one embodiment, the width of the gantry 40 (W) is less than about 17 inches, and can be about 15 inches or less.

Figure 3B:
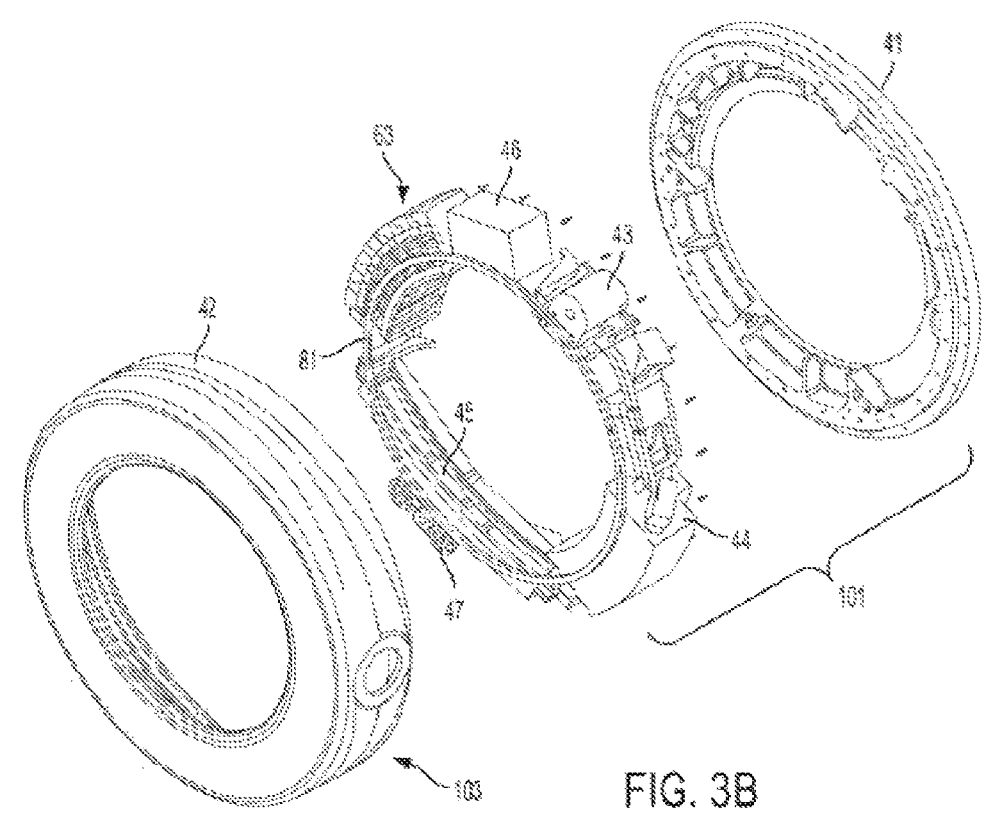
FIG. 3B is an exploded view of the imaging system of FIG. 3A.

A number of features of the various embodiments may facilitate the compact size of the imaging gantry 40. For example, as previously discussed the outer shell 42 of the gantry 40 may be a relatively thin yet rigid exoskeleton structure that provides a protective outer covering for the rotating components while simultaneously supporting the rotating components in multiple dimensions as they rotate relative to the outer shell 42. Various additional features are illustrated in FIG. 4F, which illustrates the rotating portion 101 of the imaging system 100 according to one embodiment. The various components, such as x-ray source 43, detector 45, high-voltage generator 44, heat exchanger 430, computer 46, battery system 63, docking system 35 and rotor driver 47, may be mounted to rotor 41 and configured to fit and rotate within the internal cavity 418 of the gantry 40 shown in FIG. 4E. As shown in FIGS. 3A and 4F, for example, this may include providing the drive mechanism 47 within the interior cavity 418 of the gantry 40, which may aid in minimizing the outer diameter and width dimensions of the gantry 40 while also enabling a relatively large bore diameter. Various other components may be configured to facilitate a compact gantry design. For example, as shown in FIG. 4F, the high-voltage generator 44, which may be one of the larger components of the rotating portion 101, may have at least one surface 432, 434 that is angled or curved to substantially correspond with the curvature of the gantry 40 and/or bore 416. Another example of a high-voltage generator 44 with an angled or curved outer surface is shown in FIGS. 3A-B. Similarly, the battery system 63 may be housed in a chassis having at least one surface 436, 436 that is angled or curved to substantially correspond with the curvature of the gantry 40 and/or bore 416. In this way, the outer diameter of the gantry may be minimized while also maintaining a relatively large bore diameter.

The imaging system 100 generally operates in a conventional manner to obtain images of an object located in the bore of the gantry. For example, in the case of an x-ray CT scan, the rotor 41 rotates within the housing of the gantry 40 while the imaging components, including the x-ray source and x-ray detector, obtain image data at a variety of scan angles. Generally, the system obtains image data over relatively short intervals, with a typical scan lasting less than a minute, or sometimes just a few seconds. During these short intervals, however, a number of components, such as the x-ray source tube and the high-voltage generator, require a large amount of power, including, in some embodiments, up to 32 kW of power.

In one embodiment, the power for the rotating portion 101 of the system 100 is provided by a battery system 63 that is located on the rotating portion 101 of the system 100. An advantage of the battery-based power supply is that the conventional schemes for delivering power to the imaging components, such as complicated and expensive slip-ring systems and bulky cable systems, can be avoided.

As shown in FIGS. 3A and 3B, the battery system 63 is mounted to and rotates with the rotor 41. The battery system 63 includes a plurality of electrochemical cells. The cells can be incorporated into one or more battery packs. In one embodiment, for example, the battery system 63 includes seven battery packs 64, with sixty-four cells per pack 64, for a total of 448 cells. The battery system 63 is preferably rechargeable, and is recharged by the charging system 34 when the rotor 41 is not rotating. In one embodiment, the battery system 63 consists of lithium iron phosphate (LiFePO$_4$) cells, though it will be understood that other suitable types of batteries can be utilized.

The battery system 63 provides power to various components of the imaging system 100. In particular, since the battery system 63 is located on the rotating portion 101 of the imaging system 100, the battery system 63 can provide power to any component on the rotating portion 101, even as these components are rotating with respect to the non-rotating portion 103 of the imaging system 100. Specifically, the battery system 63 is configured to provide the high voltages and peak power required by the generator 45 and x-ray tube 43 to perform an x-ray imaging scan. For example, a battery system may output ~360V or more, which may be stepped up to 120 kV at a high-voltage generator (which may also be located on the rotating portion 101) to perform an imaging scan. In addition, the battery system 63 can provide power to operate other components, such as an on-board computer 46, the detector array 45, and the drive mechanism 47 for rotating the rotor 41 within the gantry 40.

Each of the battery packs 64 includes an associated control circuit 66, which can be provided on a circuit board. In certain embodiments, the control circuits 66 can communicate with one another and/or with a main battery controller that is also located on the rotating portion 101 of the imaging system 100.

Figure 5:
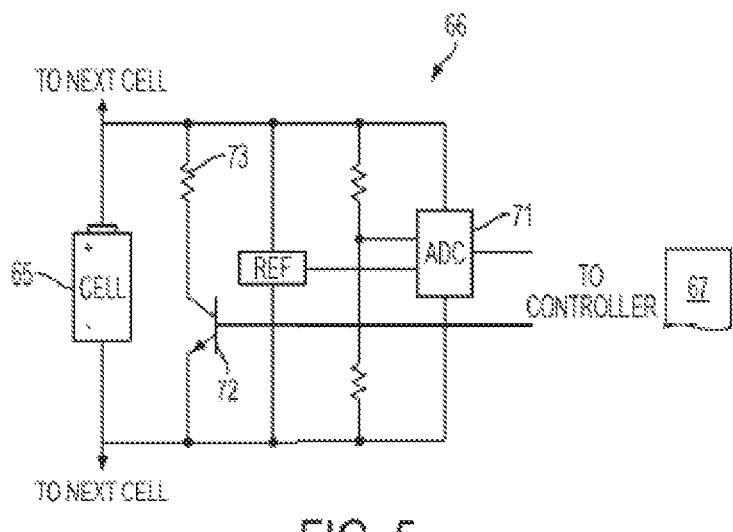
FIG. 5 illustrates a battery pack control circuit according to one embodiment of the invention.

The battery pack control circuit(s) 66 are configured to monitor and/or alter the state of charge of each of the electrochemical cells 65 in the battery pack 64. An example of a battery pack control circuit 66 is shown in FIG. 5. In this embodiment, the control circuit 66 connects across each individual cell 65. The control circuit 66 monitors the voltage of the cell 65, and generates signals from the analog-to-digital converter 71 that indicate the charge-state of the cell. These signals are provided to the main battery controller 67, which monitors the charge-state of all the cells in the battery system. The controller 67 may comprise a processor having an associated memory that may execute instructions (e.g. software) stored in the memory. The main battery controller 67 can send control signals to the respective control circuits 66 to alter the state of charge of each electrochemical cell 65. In the embodiment of FIG. 5, the main battery controller 67 alters the charge-state of the cell 65 by switching on transistor 72, which connects the cell 65 across load resistor 73. The cell 65 can then be partially drained in a controlled manner. The battery controller 67 can continue to monitor the charge state of the cell 65 and switch off the transistor 72 when the cell 65 reaches a pre-determined charge state. In one embodiment, whenever the cell 65 is in danger of overcharging, the load resistor is switched in until the battery is at a safe charge state. In certain embodiments, if an overcharge condition is actually reached in one or more cells, the charging system can be switched off while the load resistor continues to drain the cell. Other cell charging and balancing schemes can also be employed.

In certain embodiments, the battery system includes processing circuitry that is configured to implement a control scheme to cause the electrochemical cells to have substantially the same charge state. This control scheme can be implemented by a main battery controller 67, for example, or can be implemented by the plurality of battery pack control circuits 66 in communication with each another. In one exemplary embodiment of the control scheme for the battery system, a load resistor is switched in for each cell when the cell either exceeds the desired charge voltage or when the cell exceeds the average cell voltage by a predetermined threshold. The charging system is disabled if any cell exceeds the maximum charging voltage.

Figure 6A:
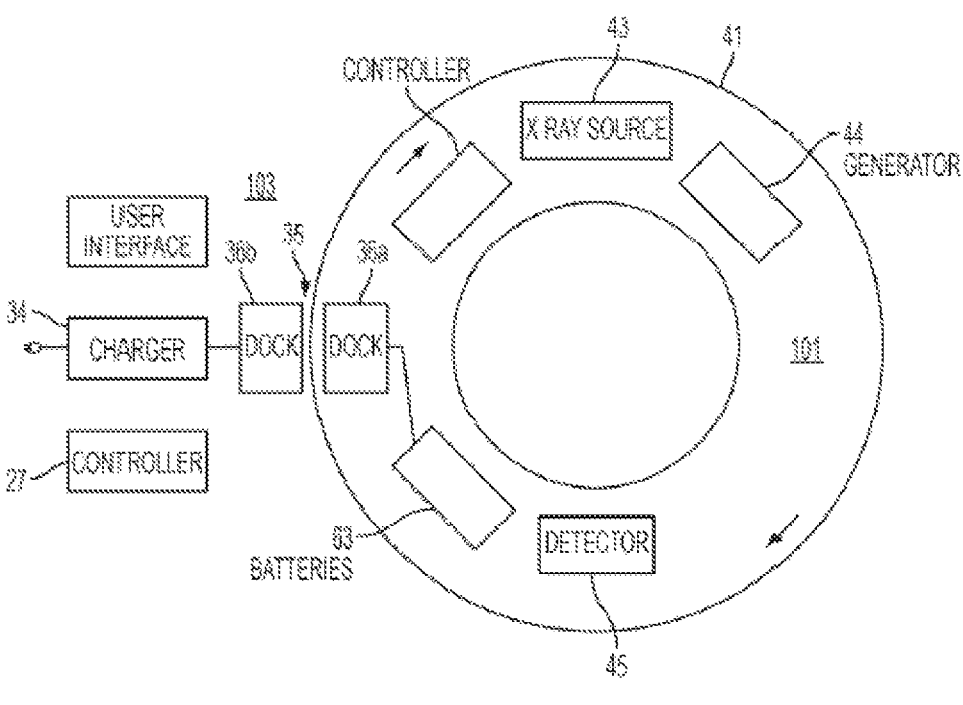
FIG. 6A is a schematic illustration of the imaging system showing the battery, charging and docking systems.
Figure 7:
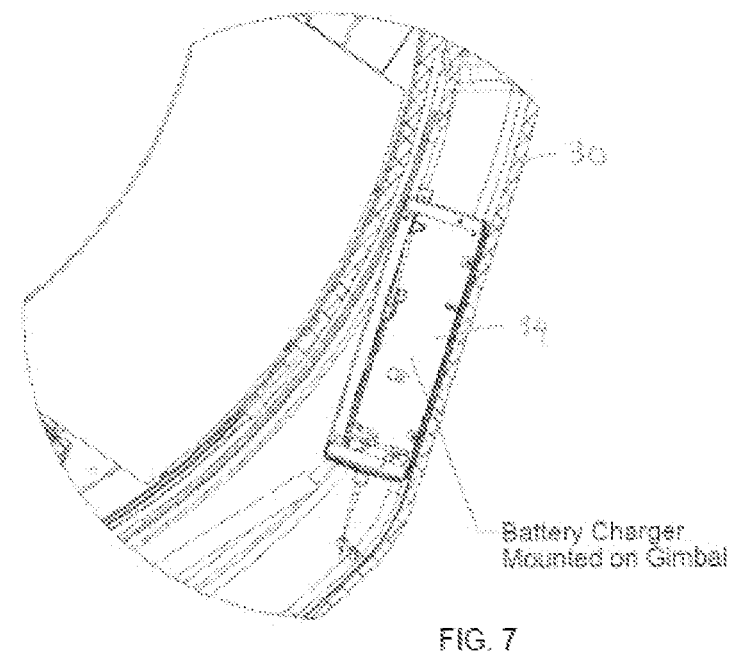
FIG. 7 is a close-up view of FIG. 3A illustrating the charging system mounted on the gimbal.
Figure 8:
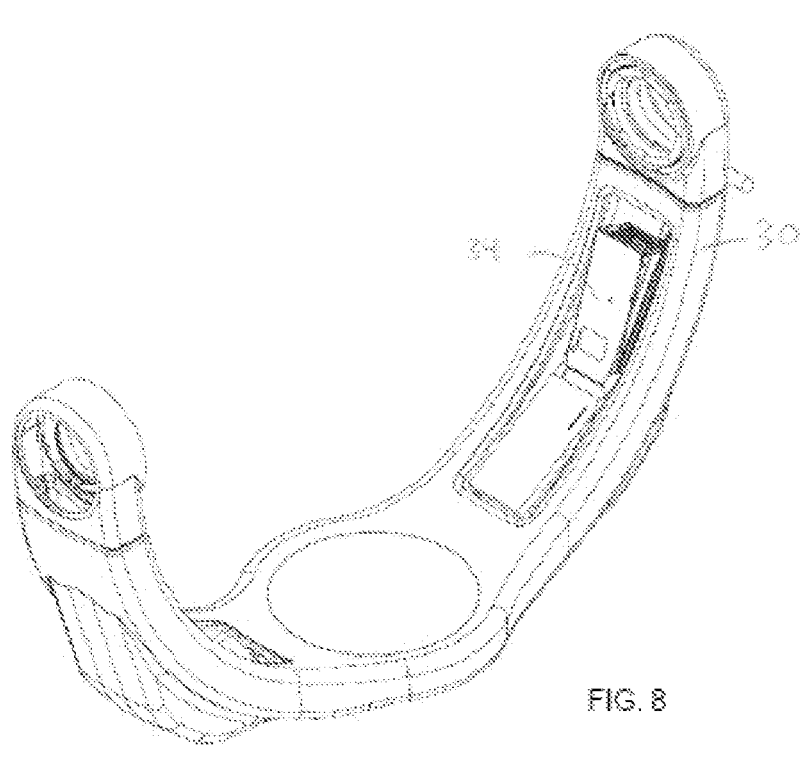
FIG. 8 is a perspective view of the gimbal with charging system.
Figure 9A:
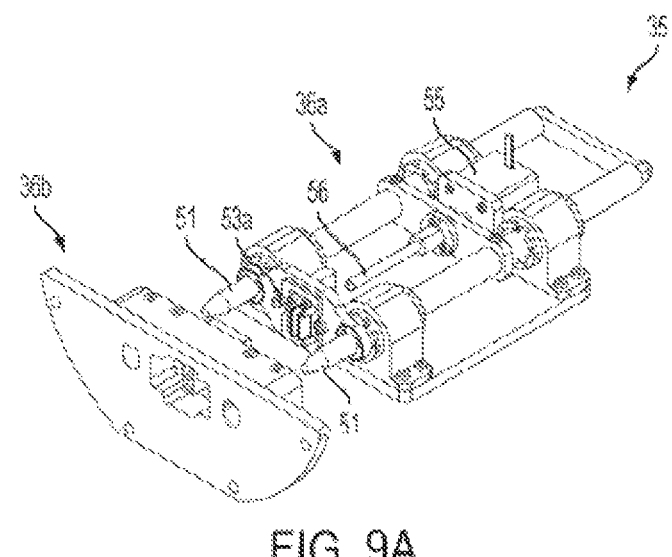
FIG. 9A is a perspective view of an embodiment of the docking system shown in a disengaged state.
Figure 9B:
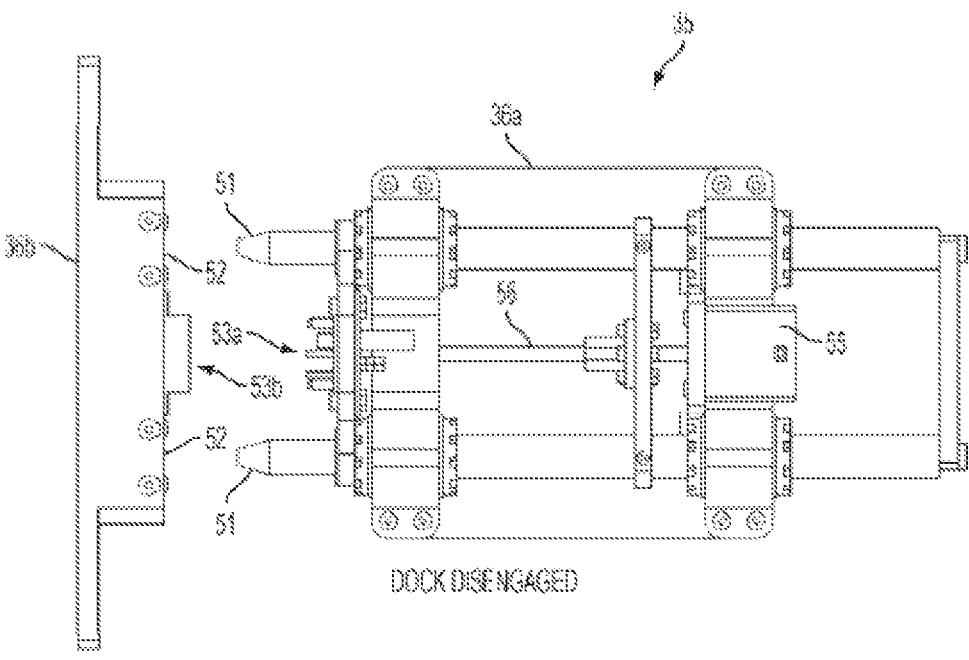
FIG. 9B is a side elevation view of the docking system in a disengaged state.
Figure 10A:
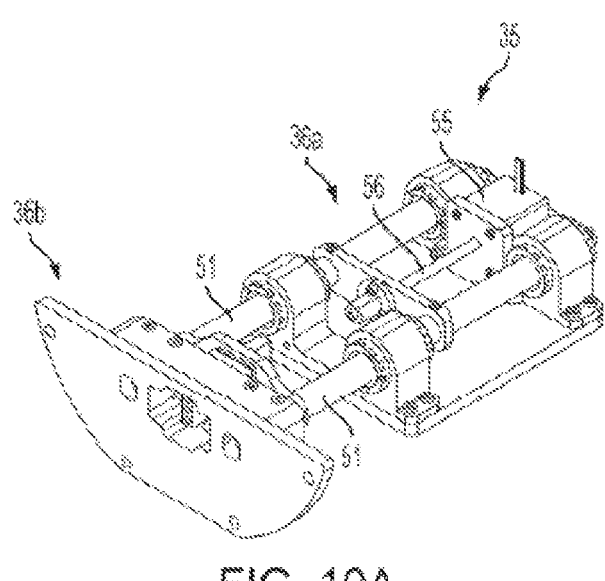
FIG. 10A is a perspective view of the docking system shown in an engaged state.
Figure 10B:
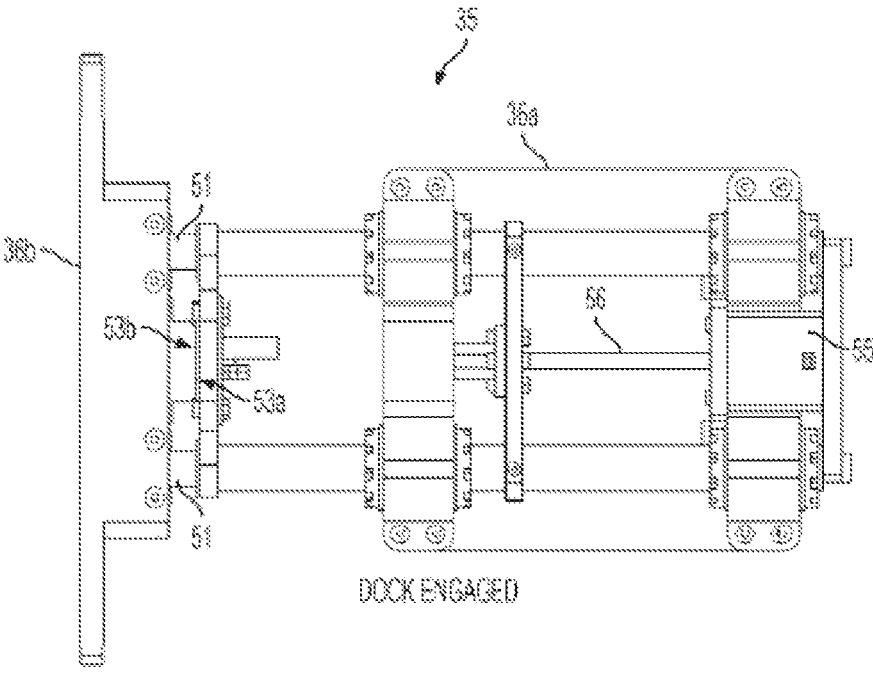
FIG. 10B is a side elevation view of the docking system in an engaged state.
Figure 11A:
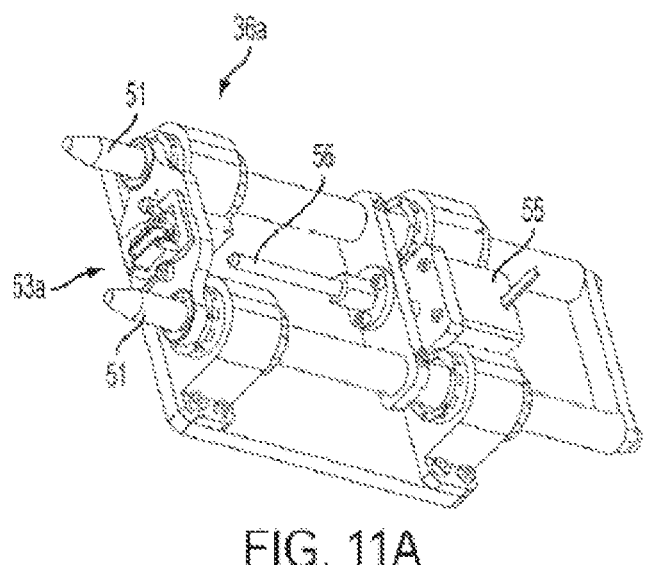
FIG. 11A is a perspective view of the portion of the docking system that is mounted to the rotor.
Figure 11B:
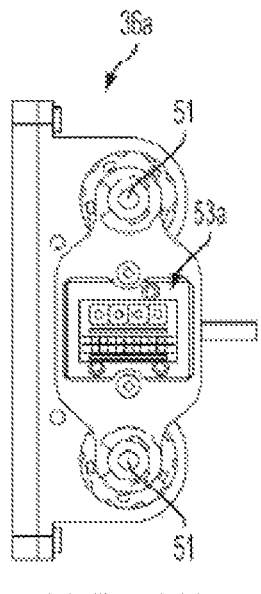
FIG. 11B is a front view of the portion of the docking system shown in FIG. 11A.
Figure 12A:
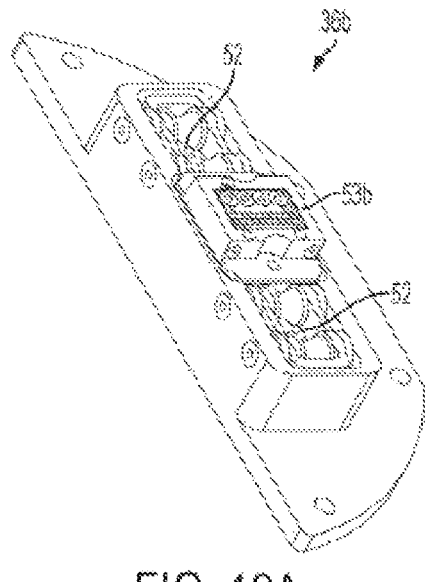
FIG. 12A is a perspective view of the portion of the docking system that is mounted to the non-rotating portion of the imaging system.
Figure 12B:
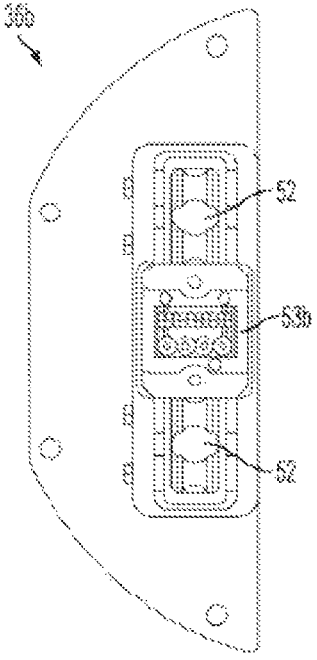
FIG. 12B is a front view of the portion of the docking system shown in FIG. 12A.
Figure 13A:
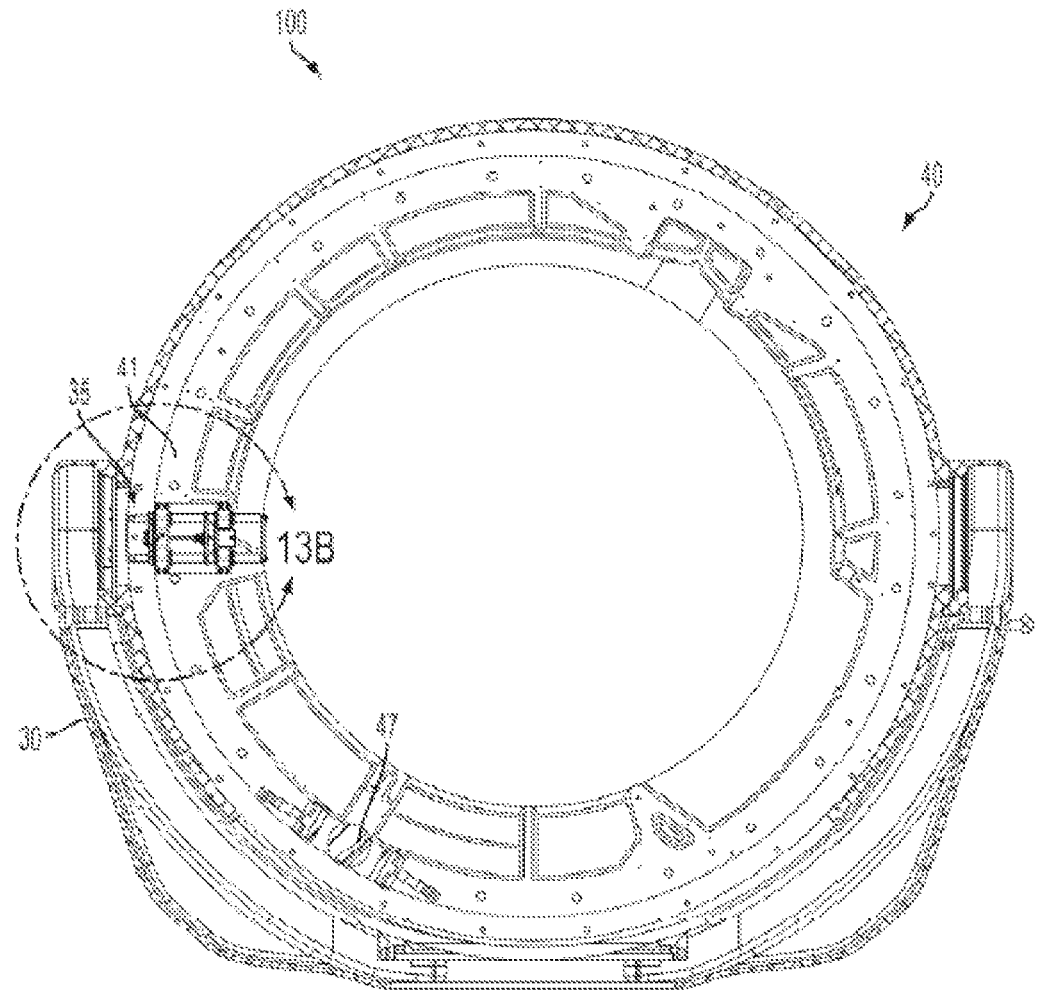
FIG. 13A is a cross-section view of an imaging system showing the location of the docking system.
Figure 13B:
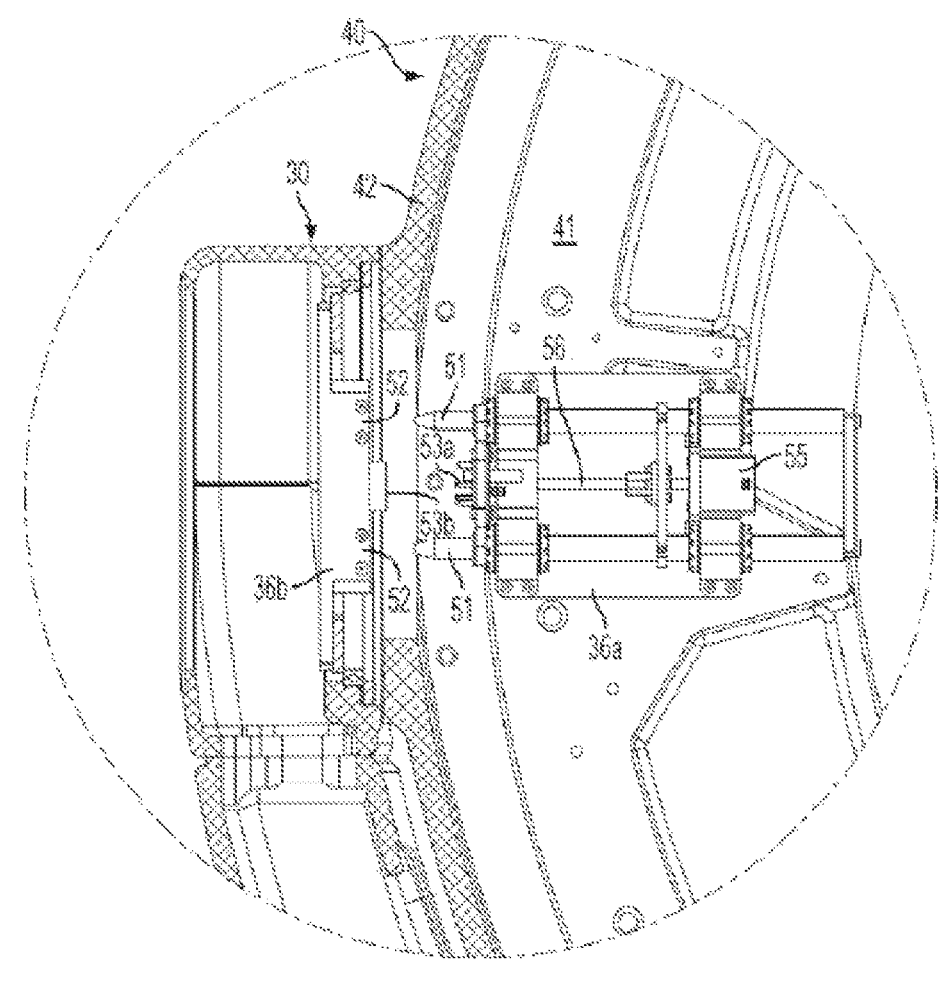
FIG. 13B is a close-up view of the docking system of FIG. 13A.

FIG. 6A schematically illustrates the battery system 63, charging system 34 and docking system 35 according to one embodiment. The charging system 34 provides electrical power to the battery system 63 in order to charge the rechargeable electrochemical cells. In a preferred embodiment, the charging system 34 is located on the non-rotating portion 103 of the imaging system 100. For example, the charging system 103 can be located on the gimbal 30, the outer shell 42 of the gantry 40, the base 20 or the pedestal 50 (see, e.g., FIGS. 1-3B). In a preferred embodiment, the charging system 34 is located on the gimbal 30. FIGS. 3A, 7 and 8 illustrate one embodiment of a charging system 34 that is located on the gimbal 30. The charging system 34 is electrically coupled to the battery system 63 at least during the times when the rotating portion 101 of the imaging system 100 is stationary relative to the non-rotating portion 103, such as in between imaging scans. The charging system 100 need not be, and in preferred embodiments is not, electrically coupled to the rotating portion 101 during an imaging scan. In one embodiment, the docking system 35 couples the charging system 34 to the battery system 63 when the rotating portion 101 is in a stationary or "park" mode, as is described in greater detail below.

The charging system 34 is configured to receive input power from an external power source, such as a standard wall power outlet. The charging system 34 can include circuitry that conditions the input power to render it suitable for recharging the battery packs 64 on the rotor 41. The charging system 34 can also include control circuitry that communicates with the battery pack control circuit(s) and controls the operation of the charging system.

In one embodiment, the charging system 34 is configured to automatically begin charging of the battery system 63 when the charging system 34 is electrically coupled to the battery system 63. During the charging operation, the battery pack control circuits 66 and/or the main battery controller 67 monitor the state of charge of the individual cells 65, and can instruct the charging system 34 to terminate charging when a pre-determined charge-state is reached. For example, charging can terminate when one or more of the electro-chemical cells 65 reach a full state of charge.

The docking system 35 is configured to selectively couple and de-couple the rotating 101 and non-rotating 103 portions of the imaging system 100. As schematically illustrated in FIG. 6A, a first portion 36a of the docking system 35 is located on the rotating portion 101 of the system, preferably on the rotor 41, and includes a mating surface that faces towards the outer circumference of the gantry 40. A second portion 36b of the docking system 35 is located on the non-rotating portion 103 of the system, such as on the gimbal 30, and includes a mating surface that faces into the interior housing of the gantry. When the system is in "park" mode, the rotor 41 automatically rotates to a position where the first 36a and second 36b portions of the docking system 35 are aligned and facing one another. Mating features (e.g., pin(s) and socket(s)) on one or both of the first 36a and second 36b portions of the docking system are actuated to physically connect the two portions 36a, 36b. During an imaging scan, the two portions 36a, 36b disengage from each other, and the first portion 36a rotates with the rotor 41 inside the interior housing of the gantry 40.

The docking system 35 includes at least one electrical connection for providing power to components on the rotating portion 101, including the rechargeable battery system 63. When the docking system 35 is disengaged, such as during an imaging scan, power for the components of the rotating portion 101 comes from the battery system 63. Components on the non-rotating portion 103 of the imaging system 100 can remain powered by an external power source, such as grid power.

In one embodiment, the docking system 35 further includes at least one electrical connection for data transfer between the rotating and non-rotating portions of the imaging system 100. The rotating portion 101 of the imaging system 100 obtains imaging data at the detector array 45, and this data may be transferred off the rotating portion 101 via the docking system 35 for processing and/or display. In one embodiment, the rotating portion 101 of the imaging system 100 includes a computer 46 having a memory and processor. The image data obtained at the detector 45 may be sent to the computer 46 for temporary storage and optional processing while the rotating portion 101 is rotating. Following an image scan, the rotating and non-rotating portions of the system are connected by the docking system 35, and the data from the on-board computer 46 may be downloaded off the rotating portion 101 for further processing and/or display.

An embodiment of a docking system 35 is shown in FIGS. 9A-14B. The first portion 36a of the docking system 35 includes a pair of moveable rods 51 that reciprocate between a first, disengaged position (FIGS. 9A and 9B) and a second, engaged position (FIGS. 10A and 10B). The first portion 36a is shown in FIGS. 11A and 11B. An electrical connector 53a is secured between the rods 51 and moves with the movement of the rods. An actuator, which in this embodiment includes a motor 55 and lead screw 56, drives the movement of the rods 51 and connector 53a. The second portion 36b of the docking system 35 is illustrated in FIGS. 12A and 12B, which shows a pair of slots 52 and an electrical connector 53b that is configured to mate with the connector 53a on the first portion 36a. During engagement of the docking system 35, the rods 51 from the first portion 36a move into engagement with the corresponding slots 52 in the second portion 36b of the docking system. This engagement prevents the rotating portion 101 from moving relative to the non-rotating portion 103 while the docking system is engaged. The rods 51 and slots 52 also ensure that the respective electrical connectors 53a, 53b on the first and second portions 36a, 36b are properly aligned as the actuator mechanism 55, 56 moves the connectors 53a, 53b into mating engagement. When the docking system 35 is engaged (FIGS. 10A and 10B), the connectors 53a, 53b carry electrical power to charge the battery system, and also enable data and control signals to pass between the rotating and non-rotating portions of the system.

Figure 14A:
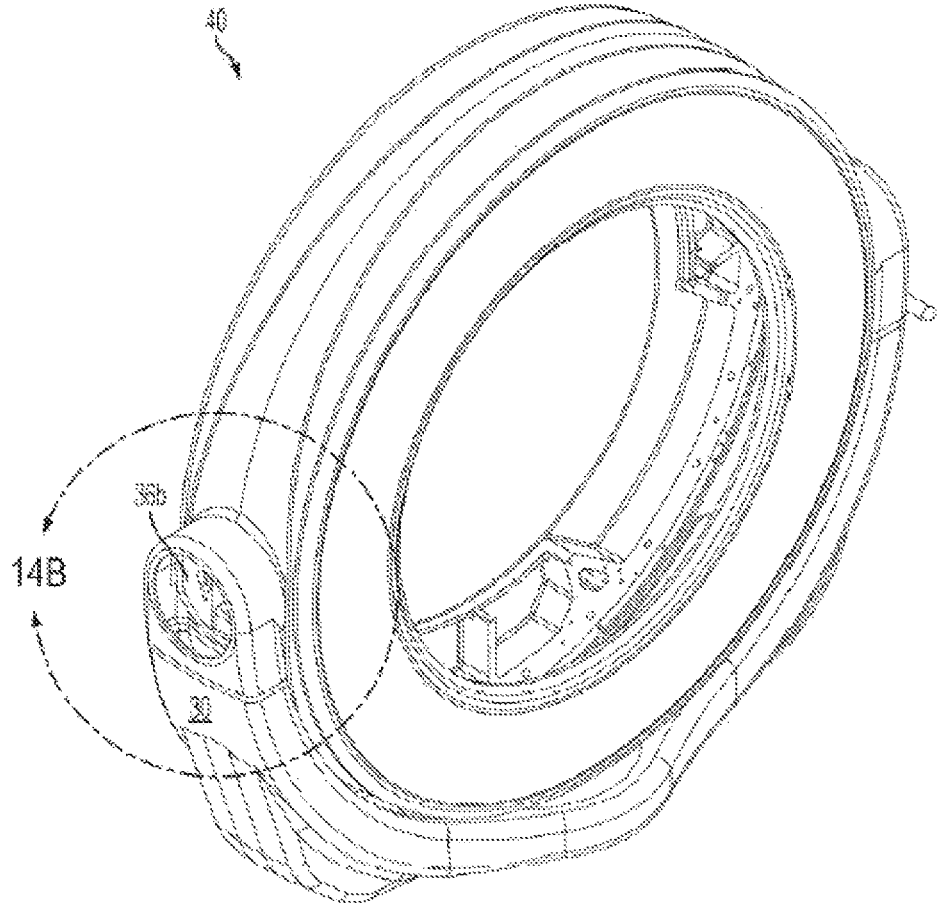
FIG. 14A is a perspective view of an imaging system showing the location of the docking system.
Figure 14B:
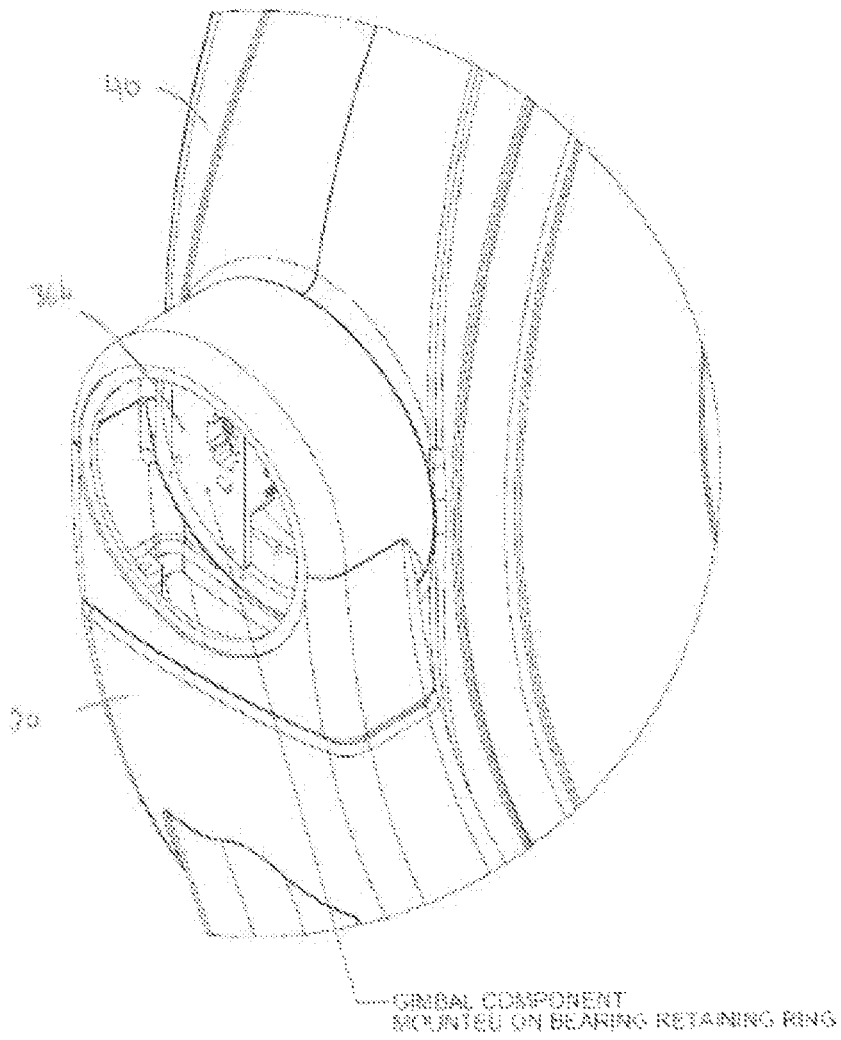
FIG. 14B is a close-up view of the docking system of FIG. 14A.

FIGS. 13A-14B illustrate the location of the docking system 35 within the imaging system 100. As seen most clearly in FIG. 13B, the first portion 36b is mounted to and rotates with the rotor 41. Between scans, the rotor 41 rotates to the "park" position of FIG. 13, and the docking system 35 is engaged. The second portion 36b of the docking system 35 is located on the gimbal 30, as shown in FIGS. 14A-B. In a preferred embodiment, the second portion 36b is mounted to the bearing on the gimbal that allows the gantry to tilt with respect to the gimbal, such that the second portion 36b rotates with the tilting motion of the gantry, which allows the docking system to dock and undock while the gantry is tilted.

In one embodiment of a docking sequence, the control circuitry on the rotor 41 causes the rotor drive mechanism 47 to rotate the rotor to the "park" position, preliminary to docking. Then, the control circuitry causes the actuator mechanism 55, 56 to drive the rods 51 (fast) to the point where the tapered end portions of the rods 51 (see, e.g., FIGS. 9A-B) engage with "rollers" that define the slots 52 on the second portion 36b of the docking mechanism. Then, the control parameters of the rotor drive mechanism are relaxed such that it can be back driven. The mating electrical contacts are then prepared to engage such that they are protected from damage during docking, as is discussed further below. Next, the rods 51 are driven (slow) to the "docked" position whereby the tapered portion of the rods pushes the rotor into alignment through contacting the rollers on the mating dock. The control circuitry then reads a loopback signal on the dock to determine proper engagement, and once proper engagement is determined, the electrical connections (e.g., power and data connections) between the rotating 101 and non-rotating 103 portions of the system are engaged. Rotor drive control parameters are then restored, and the position is assigned within the control software.

Figure 6B:
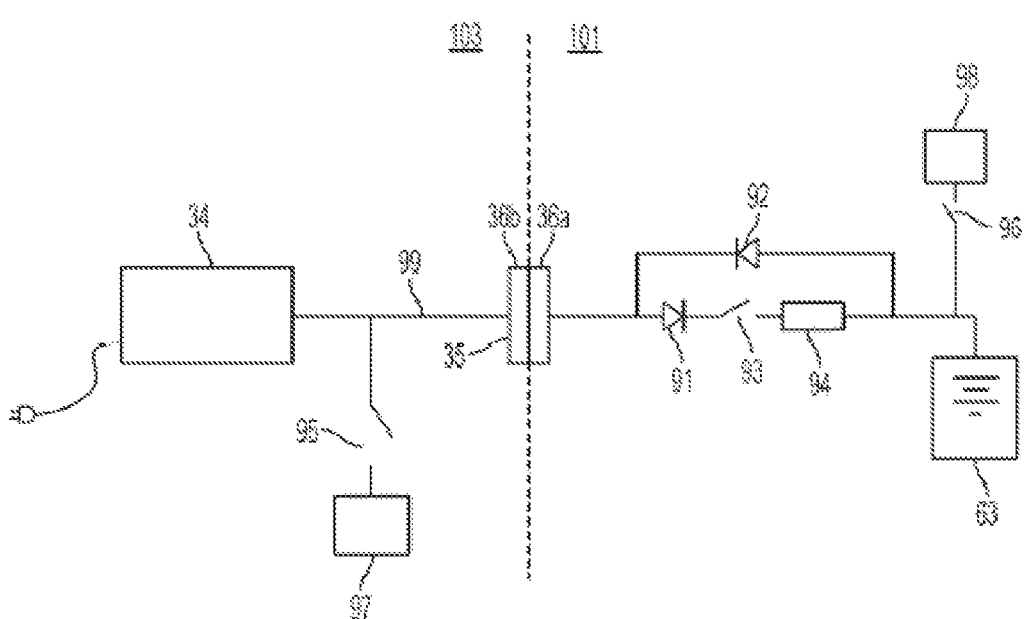
FIG. 6B schematically illustrates the power circuitry during a docking procedure of the system according to one embodiment.

FIG. 6B is a schematic illustration of the system power circuitry during a docking procedure, according to one embodiment. The system is shown in a docked configuration, with the components on the non-rotating portion 103, including charger 34 and one or more device(s) 97, which branch off a main power bus 99, electrically connected to the components on the rotating portion 101, including battery 63 and one or more device(s) 98, via docking system 35. To un-dock the system, the electrical connection between the rotating 101 and non-rotating 103 components must be broken. However, at the voltages and currents used by the system, as the respective contacts physically separate, the electricity will continue to flow briefly across the gap, forming a spark. This spark tarnishes and erodes the contacts over time, and in some cases can weld the contacts together.

There is a similar problem when the system re-docks. If the voltages on each side of the docking system are significantly different, large currents may flow through the dock as the two sides of the power system equalize. These currents can overheat the contacts.

In one embodiment, both of these problems are solved by designing and operating the system so that the voltage on the non-rotating 103 (charger) side is higher than the voltage on the rotating 101 (battery) side whenever the dock is being mated or unmated. That guarantees that current can only flow in one direction through the dock. Then, before the mating or unmating procedure is performed, a switch 93, which can be a solid-state relay (SSR), is opened to prevent current flow in that direction (i.e. from the non-rotating to the rotating side). The docking system 35 can then be safely docked or undocked.

An inrush current limiting circuit 94, which can comprise an NTC resistor, for example, is provided in series with the relay 93 to protect components, including the relay(s) and the docking system 35, against damage from current inrush during a docking procedure when the relay 93 is turned on.

Note that when the system is docked, power is always free to flow from the batteries 63 to components on the non-rotating side 103 of the system via diode 92 and docking system 35. However, the rotating portion 101 cannot receive power from the non-rotating portion unless the relay 93 is switched on. The relay 93 can also be used to halt charging of the batteries in an over-charge or other emergency situation.

In practice, this configuration means that the system generally cannot be undocked while it is not plugged into the wall (i.e., the entire system is being run off the batteries) or when the main/transport drive for the system is active because this component can draw more power than the charger can source. However, neither of these cases is particularly restrictive within normal use of the system.

The systems can include additional safety/failsafe features, such as relays 95, 95 to protect the various device component(s) 97, 98 on both the non-rotating and rotating sides 103, 101 of the system. For example, in the case where the non-rotating portion 103 loses power during a scan (i.e. with the system un-docked), the system can be configured so that all the relays 95 on the non-rotating portion 103 automatically turn off, so that the non-rotating portion 103 is essentially electrically inert when, after the scan, the rotating portion 101 re-docks. Similar relays 96 can be provided on the rotating portion 101, for example, to selectively turn off components 98.

In certain embodiments, data transfer between the rotating 101 and non-rotating 103 portions of the imaging system 100 can be accomplished using a slip ring system. With the slip ring system, continuous electrical contact is maintained between the stationary and rotating parts of the imaging system 100. In one embodiment, a conductive ring is positioned on the outer circumference of the rotating portion 101 and electrical contacts, such as conductive brush(es), are located on the non-rotating portion 103 and maintain continuous contact with the rotating portion 101 during imaging. During an imaging scan, data is transferred from the rotating to the non-rotating portions via the slip ring in real-time. Power to the rotating portion 101 can be provided through the docking system 35 to the rechargeable battery system 63, as described above. The slip ring system can therefore be optimized for high-speed data transfer. The slip ring system in this embodiment need not be designed for high-voltage, high-power operation, which can help minimize the complexity and expense of the slip ring system. In an alternative embodiment, a cable system can be used for data transfer between the rotating and non-rotating portions. As with the slip ring embodiment, the cable system need not be designed for high-voltage, high-power operation, since primary power to the rotating portion is provided by the rechargeable battery system.

In another alternative embodiment, the rotating portion 101 can include a wireless transmitter for transmitting the data off of the rotating portion 101 via a wireless communication link. In this embodiment, the image data need not be transferred over the docking system 35 or a slip-ring or cable system.

The docking system 35 may also be used to transmit control signals between the rotating and non-rotating portions of the imaging system 100. The control signals can include, for example, signals from a main system controller 27 (FIG. 6A), located on the non-rotating portion 103 to components on the rotating portion 101, such as the x-ray source and detector, battery system and on-board computer, as well as signals from the rotating portion to the non-rotating portion, such as signals from the battery system 63 to the charging system 34 with respect to the charge state of the electrochemical cells. It will be understood that these signals can also be sent over a slip ring or cable system or by a wireless link, as described above.

As previously discussed, an advantage of the battery-based power supply of the invention is that the conventional schemes for delivering power to the imaging components, such as complicated and expensive slip-ring systems and bulky cable systems, can be avoided. In one embodiment, during an imaging scan the imaging system 100 is essentially severed in two, with two independent sub-systems (i.e., the rotating and non-rotating portions) operating independently of one another. This is different from conventional imaging systems, in which the rotating components remain physically coupled to the non-rotating portion of the system, via a cable or slip-ring or the like.

Figure 15:
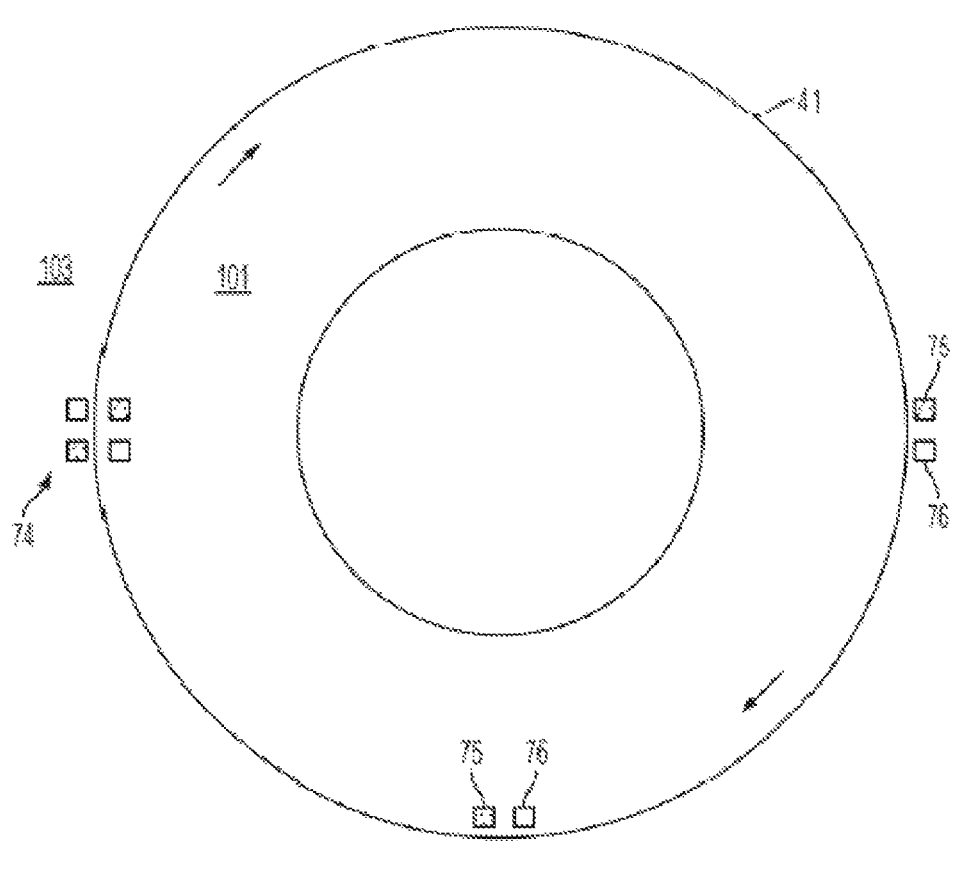
FIG. 15 illustrates a non-contact signaling apparatus according to one embodiment.
Figure 16:
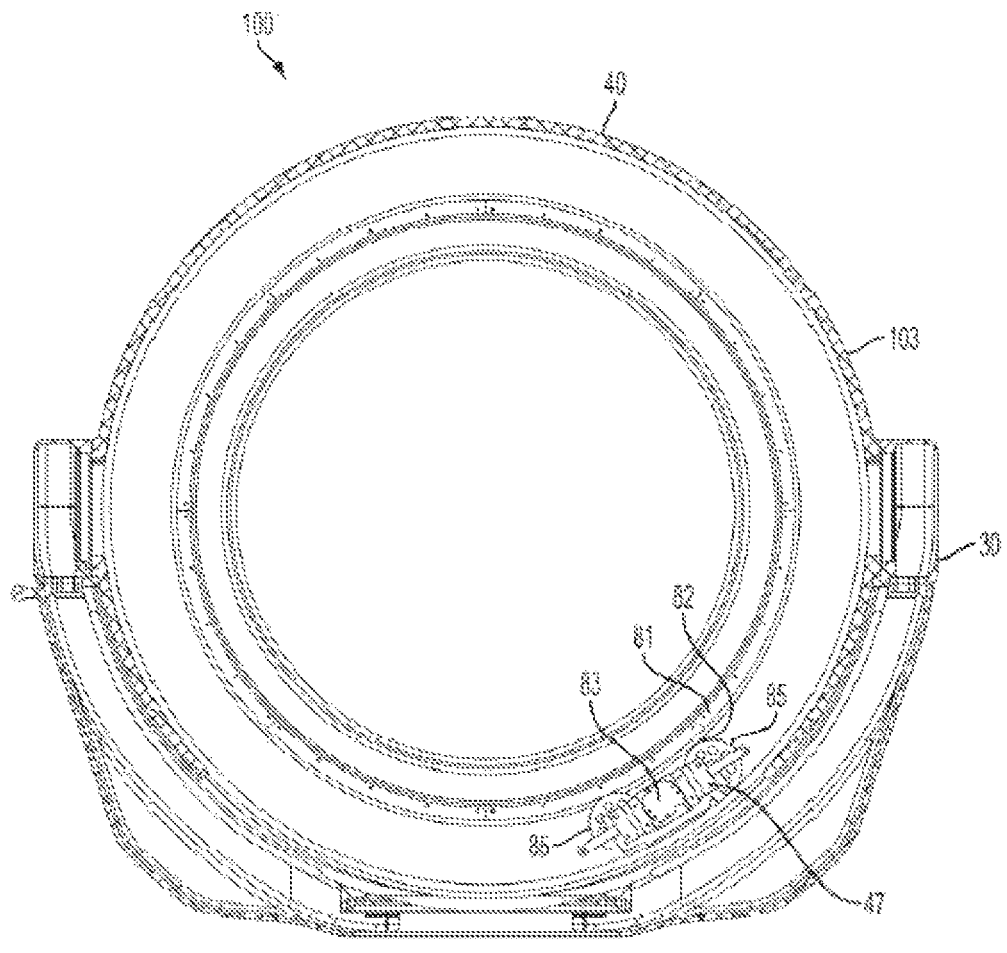
FIG. 16 is a cross-section view of an imaging system with a drive mechanism for driving the rotation of the rotor.
Figure 17:
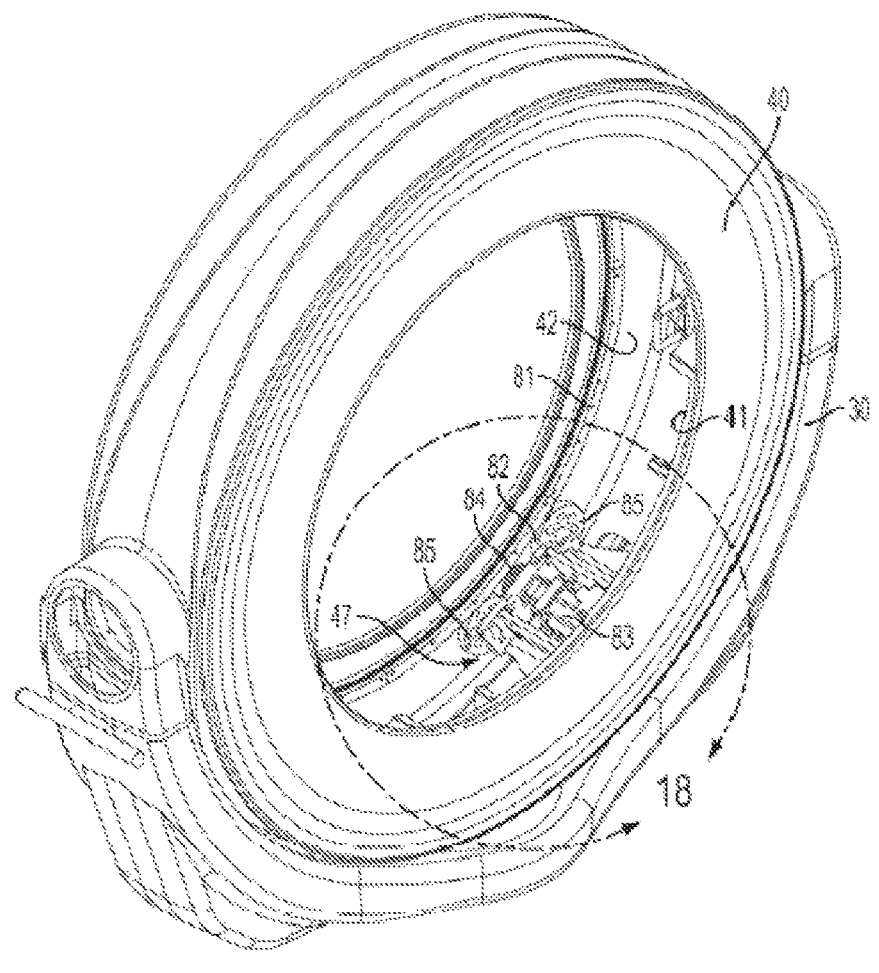
FIG. 17 is a perspective view of the imaging system illustrating the rotor drive mechanism.
Figure 18:
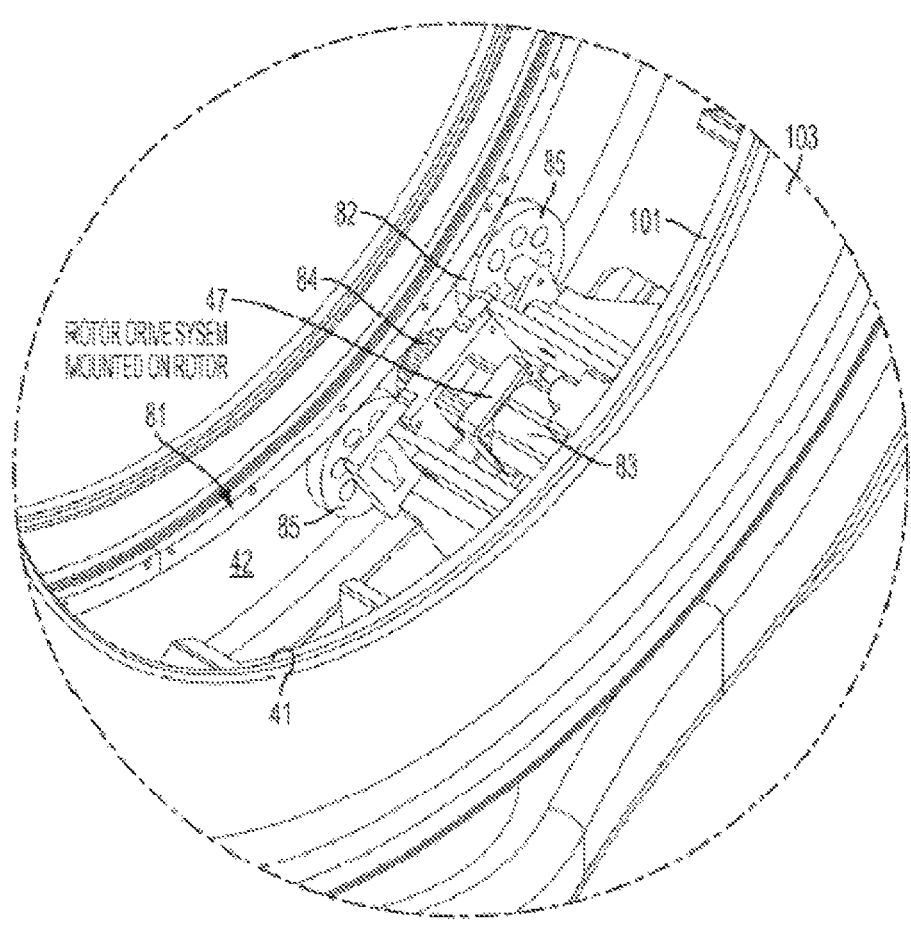
FIG. 18 is a magnified view of the rotor drive mechanism of FIG. 17.
Figure 19:
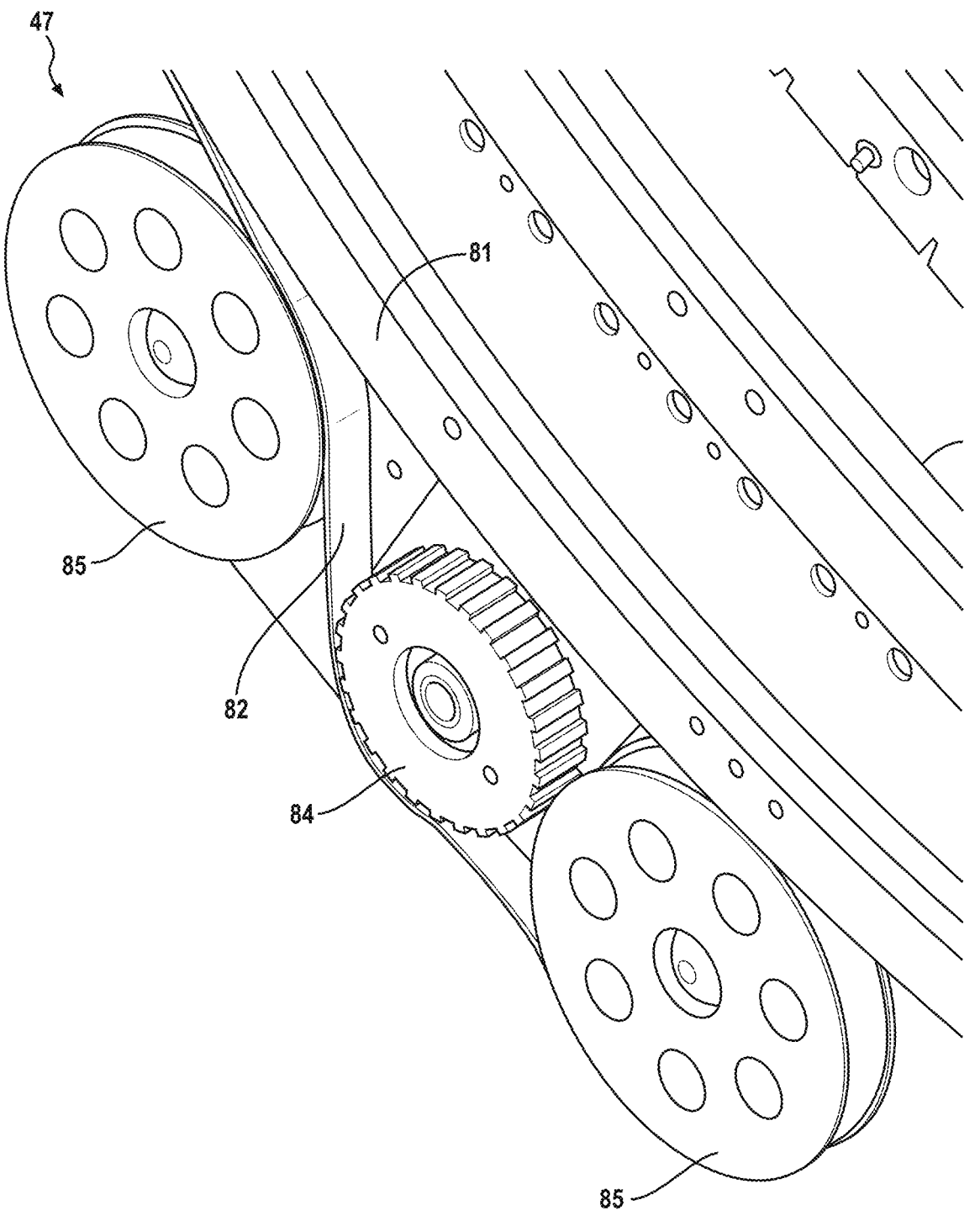
FIG. 19 is a perspective view of the drive mechanism showing a belt and motorized gear system.

In one embodiment, as shown in FIG. 15, the present invention includes a non-contact signaling apparatus 74 located at discrete positions on the rotating and non-rotating portions of the imaging system. The signaling apparatus 74 allows for minimal communication between the rotating and non-rotating portions of the imaging system. In one aspect, the signaling apparatus 74 functions as a safety mechanism. For example, during an imaging scan, the signaling apparatus 74 on the non-rotating portion 103 communicates a signal to the rotating portion 101, instructing the rotating portion 101 to continue the scan. This periodic signaling from the non-rotating portion to the rotating portion enables the scan to continue. However, if for any reason the scan needs to be terminated (such as due to a loss of power or because of a patient or clinician safety issue), the signaling apparatus 74 ceases communication of these "enable scan" signals. This lack of a signal causes the rotating component to immediately terminate the scan, without having to wait for the rotating portion to fully complete the scan and return to the docking position.

The signaling apparatus 74 can also be used to provide a signal from the rotating to the non-rotating portions to continue the scan. For example, if there is a malfunction on the rotating portion of the system (e.g., the x-ray generator fails to produce radiation, the rotor fails to rotate properly, etc.), it does not make sense for the non-rotating components to continue with the scan. In this embodiment, the scan is automatically terminated when the rotating portion stops sending signals to the non-rotating portion via the signaling apparatus 74.

In some embodiments, the signaling apparatus 74 may be used to transmit synchronization information from the rotating portion 101 to the non-rotating portion 103 of the imaging system. For example, a signaling apparatus 74 on the rotating portion 101 may communicate a signal to the non-rotating portion 103 to assist in coordinating various functions between the two portions. In one example, the signaling apparatus 74 may be used to coordinate a z-axis translation of the gantry 40 relative to the patient with the rotational motion of the rotor 41. Since the two halves of the imaging system become physically disconnected during a scan, this allows for the two halves to coordinate when they are going to start a scan sequence. A typical sequence is for the docking system to disconnect, the rotor to start accelerating, and then a signal is sent from the rotating portion to the non-rotating portion via the signaling apparatus 74 to trigger the start of the z-axis translation.

The non-contact signaling apparatus 74 may use, for example, optical or magnetic signals. One embodiment of the signaling apparatus 74 is schematically illustrated in FIG. 15. In this embodiment, the non-contact signaling apparatus 74 employs optical signaling, and includes light-emitting diodes (LEDs) 75 and photo-detectors 76 at discrete positions on the rotating 101 and non-rotating 103 portions of the imaging system. Two sets of signaling devices, each set consisting of an LED 75 and a photo-detector 76, are located on the non-rotating portion 103 of the imaging system 100, such as on the gantry 40 or the gimbal 30. Two additional sets of signaling devices, each also consisting of an LED 75 and photo-detector 76, are located on the rotating portion 101 of the imaging system 100, and in particular, on the rotor 41. The two sets of signaling devices on the non-rotating portion 103 are on opposite sides of the gantry 40; i.e., separated by 180 degrees. The two sets on the rotating portion 101 are separated by 90 degrees. In this way, the rotating 101 and non-rotating 103 portions of the imaging system 100 may exchange signals with one another at every 90 degrees of rotation of the rotating portion 101.

According to another aspect, the imaging system 100 includes a rotor drive mechanism 47, as shown in FIGS. 3A, 3B and 4F, which drives the rotation of the rotating portion 101 relative to the non-rotating portion 103. One embodiment of the rotor drive mechanism 47 is illustrated in FIGS. 16-19. In this embodiment, the rotor 41 is driven by an internal belt drive. The belt 82 extends around the outer circumference of a circular railing 81. The railing 81 (which can be seen in the exploded view of FIG. 3B and in FIG. 4F) is mounted to an interior wall of the outer shell 42 of the gantry 40. The drive mechanism 47 includes a motor 83, gear 84 and rollers 85, and is mounted to the rotor 41. The belt 82 is looped through the drive mechanism 47, running between each of the rollers 85 and the railing 81, and over the gear 84, as is most clearly illustrated in FIGS. 18 and 19. (When viewed from the side, the path of the belt 82 through the drive mechanism 47 somewhat resembles the Greek letter omega, Ω). The gear 84 is driven by the motor 83. As the gear 84 rotates, it meshes with the belt 82, which is held against the railing 81 by the rollers 85. The rotation of the gear 84 causes the drive mechanism 47 to "ride" along the length of the belt 81, thus driving the rotation of the rotor 41, which is attached to the drive mechanism 47, around the circumference of the gantry 40.

As shown, for example, in FIGS. 3A and 3B, the drive mechanism 47 is mounted to the rotor 41 beneath the detector array 45, and opposite the x-ray source tube 43. This can be advantageous, since the motorized components of the drive mechanism 47 can result in EM interference with the tube that can affect the position of the x-ray focal spot. By placing the drive mechanism on the opposite side of the rotor 41 from the x-ray source 43, the possibility of EM interference is minimized.

As discussed above, embodiments may include a mobile imaging system, such as system 100 shown in FIG. 1, in which the gantry 40 and an optional gimbal 30 may translate with respect to the base 20 to provide an imaging scan (i.e., in an imaging mode), and the entire system, including the base 20, gantry 40 and gimbal 30 may be driven in a transport mode. In the embodiment of FIG. 1, a drive system

70 located within an open region of the base 20 and beneath the gimbal 30 and gantry 40 may provide both the translation motion of the gantry 40/gimbal 30 in an imaging mode and the translation of the entire system 100 in a transport mode.

Figure 20A:
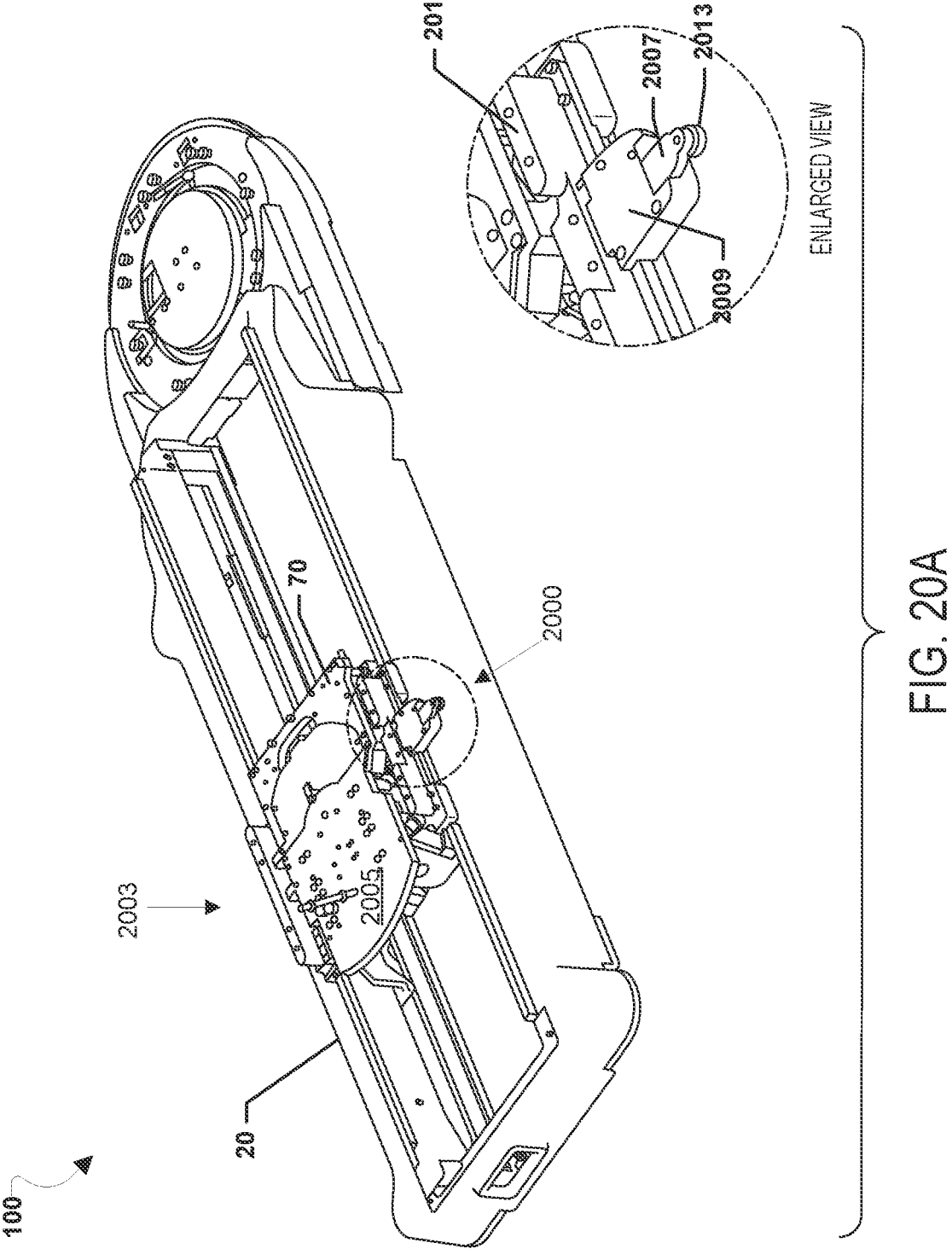
FIGS. 20A-B illustrate a latch mechanism to prevent translation of the gimbal relative to the base during transport mode.
Figure 20B:
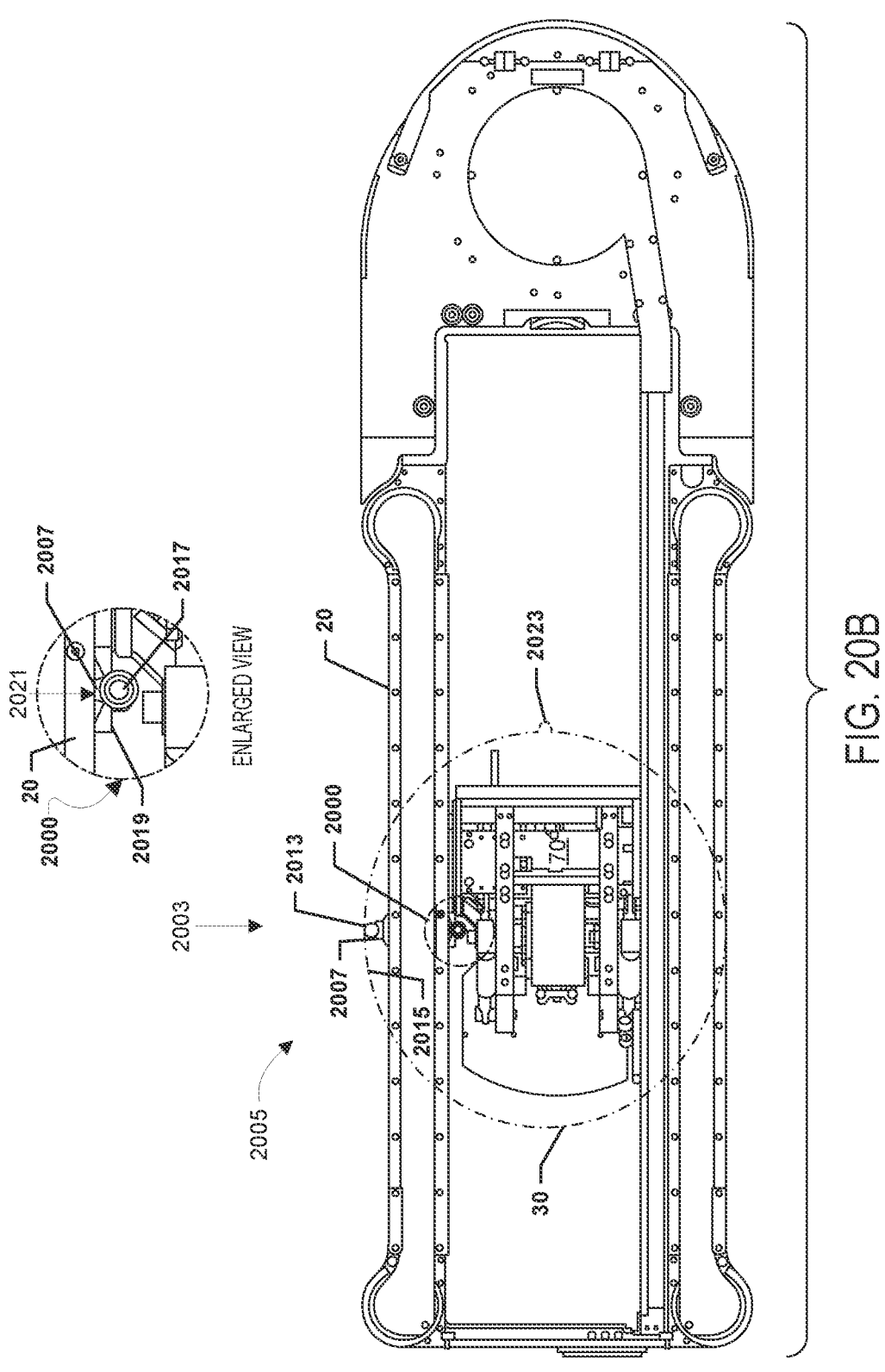

Various embodiments include a mechanism that prevents one or more components of the system 100 that translate relative to the base 20 in a scan mode (such as the gantry 40, gimbal 30 and drive mechanism 70, collectively referred to as "translating components") from translating relative to the base 20 when the system 100 is in transport mode. In one embodiment, the one or more translating components may be locked to a "transport" position to prevent the translating components from moving relative to the base 20, such as by translating up and down the rails 23 in the z-axis direction. The transport position may be located anywhere along the length of the base, such as towards the middle of the base for balance/ease of transport. FIGS. 20A-B illustrates a mechanism 2000 for locking the translating components 2005 in a transport position 2003. In various embodiments, the translating components 2005 (e.g., drive mechanism 70, gimbal 30 and gantry 40) translate relative to the base 20 during a scan mode, and at least a portion of the translating components 2005 (e.g., gimbal 30 and gantry 40) rotate relative to the base 20 to a second rotational position in a transport mode, and a latching mechanism 2000 is operable when the translating components 2005 are in the second rotational position to prohibit translation of the translating components 2005 relative to the base 20.

The latching mechanism 2000 may automatically engage when the translating components 2005 are in the second rotational position, and are translated to a transport position 2003 with respect to the base 20. The latching mechanism 2000 may not be engaged when the translating components 2005 are translated to the transport position 2003 but are not in the second rotational position. In one example, the latching mechanism 2000 engages when the translating components 2005 (e.g., gimbal 30 and gantry 40) are rotated "in line" with the base 20 and are located at, or are translated to, a discrete transport position 2003 along the length of the base 20. In embodiments, the latching mechanism 2000 may be configured such that engagement of the latch is not triggered while the system is in a scan mode (e.g., with the gimbal 30 rotated out of the "in line" position, such as where the gimbal 30 and gantry 40 are rotated generally perpendicular to the length of the base 20, or ±90° from an "in line" position, as shown in FIG. 1).

One implementation is shown in FIGS. 20A-B. The latching mechanism 2000 may include a spring-loaded slider 2007 in a guide 2009 that is connected to the gimbal 30. (In this embodiment, the block 2011 next to the slider 2007 attaches the gimbal 30 to the drive mechanism 70. For clarity, the gimbal 30 is not shown in FIG. 20A). On one end of the slider is a bearing/roller 2013. This rides on a bearing surface 2015 in the gimbal 30, as illustrated by dashed-dotted line in FIG. 20B, which is a bottom view of the system 100, looking up to the base 20, the drive mechanism 70 and the lower portion of the gimbal 30 (indicated schematically by the dashed-dotted line). The spring-loaded slider 2007 is biased towards the bearing surface 2015 of the gimbal 30 in this embodiment.

Attached to the second end of the slider 2007 is a latch 2017 (z-latch), as shown in the enlarged view of FIG. 20B. A strike plate 2019 having a slot 2021 for the latch 2017 is on the base 20, at the "transport" position 2003. During imaging, the gimbal 30 is rotated out of the "in line" configuration (see, e.g. FIG. 1), and the gimbal 30 may translate up and down the base 20, and the z-latch 2017 passes the strike plate 2019 without engaging the slot 2021. When the gimbal 30 is rotated to an in-line position, then the bearing/roller 2013 is spring-biased into a detent/slot 2023 on the bearing surface 2015 of the gimbal 30, which moves the z-latch 2017 closer to the interior side wall of the base 20. Thus, when the gimbal 30 is located at or translates to a position such that the z-latch 2017 is adjacent to the strike plate 2019, the z-latch 2017 is pushed into the slot 2021 of the strike plate 2019, locking the position of the translating components 2005 (e.g., the gimbal 30, the gantry 40 and the drive mechanism 70) with respect to the base 20. When the gimbal 30 is rotated out-of-line again, the bearing/roller 2013 rolls out of the detent 2023 and along the bearing surface 2015 of the gimbal 30, which pushes the z-latch 2017 away from the strike plate 2019 and the translating components 2005 can again translate relative to the base 20.

In embodiments, control software of the imaging system 100 may be configured to drive the translating components 2005 to the "transport" position 2003 so that the z-latch 2017 engages the strike plate 2019 whenever the system 100 enters transport mode.

Other latching mechanisms to prevent translation of the translating components 2005 relative to the base 20 during transport mode are possible, and could utilize a servo-motor, magnetic latch, etc.

In embodiments, the rotation of the gimbal 30 and gantry 40 relative to the base 20/drive mechanism 70 may be performed using a motorized system, with an encoder on the bearing that enables the gimbal 30 and gantry 40 to rotate to a selected angular position relative to base 20. In embodiments, the gimbal 30 and gantry 40 may be rotated to any arbitrary angle relative to the base 20. In other embodiments, the rotation of the gimbal 30 and gantry 40 may be performed manually.

In various embodiments, a latching mechanism (i.e., rotation latch) may maintain rotating components (e.g., the gimbal 30 and gantry 40) at a particular rotational position relative to non-rotating components (e.g., the base 20 and drive mechanism 70) of the system 100. The rotation latch may be manually controlled or servo-controlled, for example. In one embodiment, the rotation latch is cable actuated. The rotation latch may snap into place (engage) when the rotating components (e.g., gimbal 30 and gantry 40) are rotated to particular angle relative to the non-rotating components (e.g., base 20 and drive mechanism 70), and the latch may be released (disengaged) via a release mechanism. In one embodiment, the release mechanism may be located on an arm of the gimbal 30 and is linked to a lever that releases latch (e.g., via a cable).

Figure 21A:
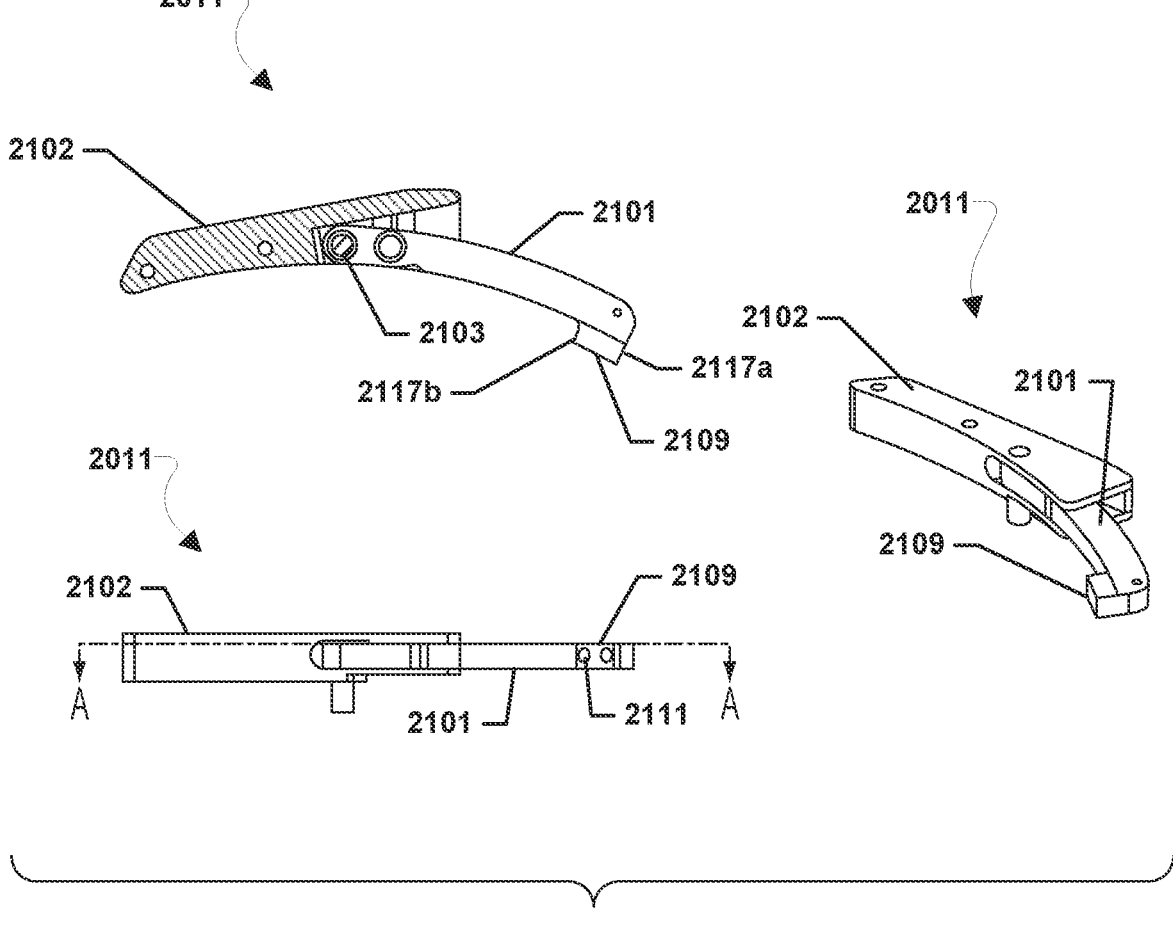
FIGS. 21A-C illustrate a rotation latch according to one embodiment.
Figure 21B:
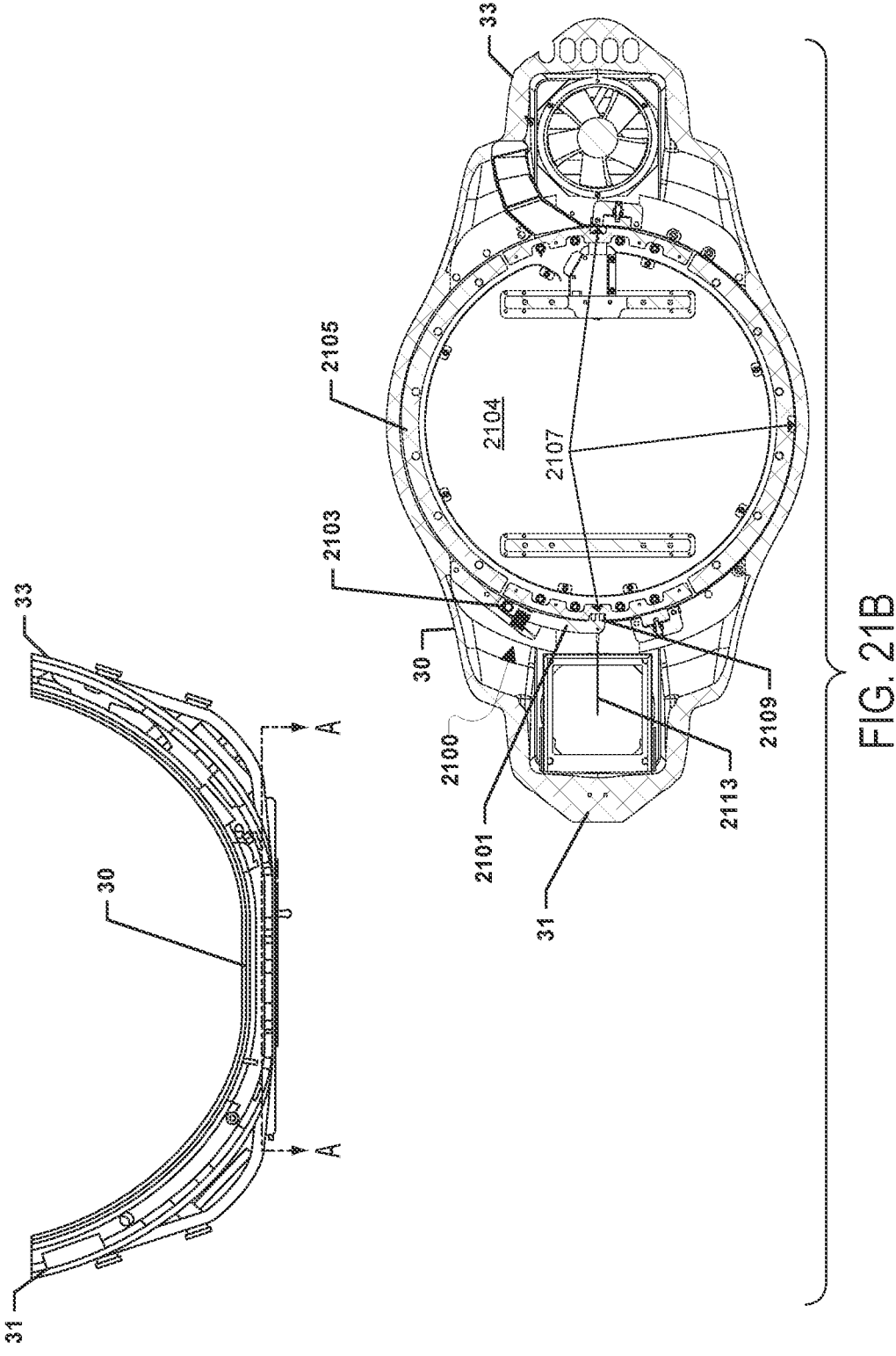
Figure 21C:
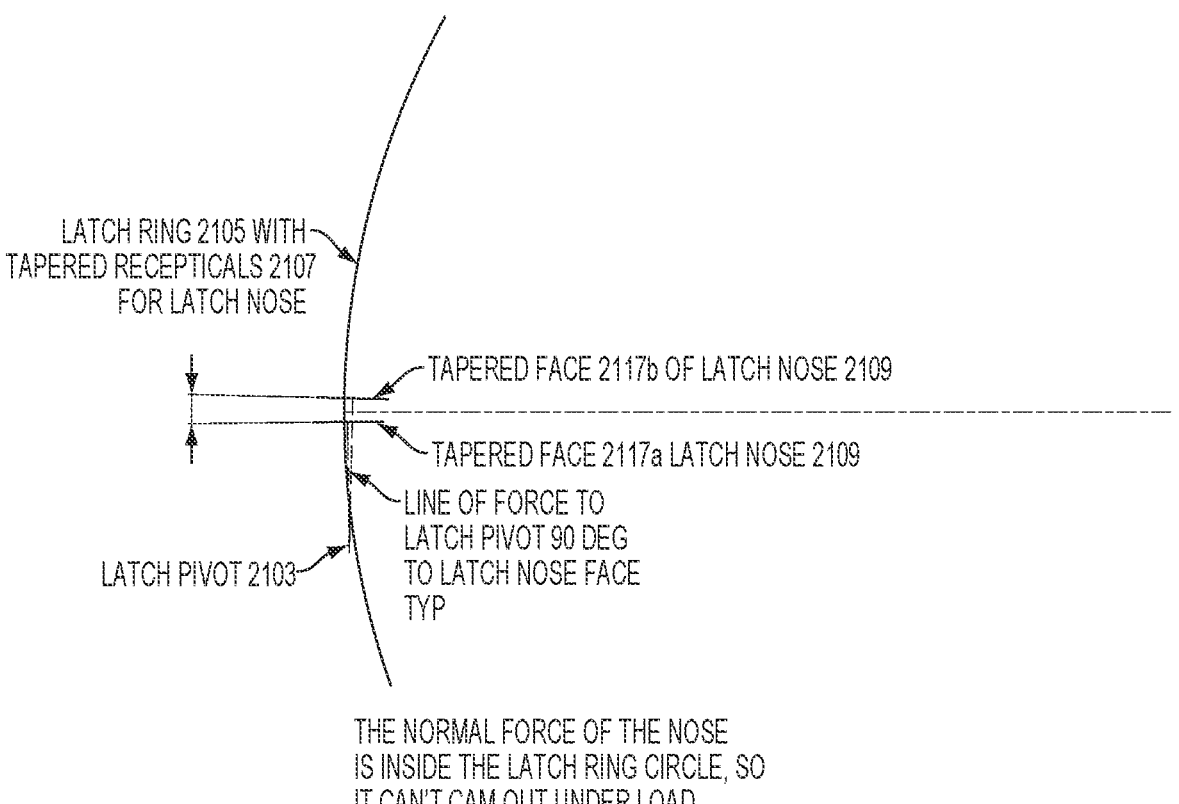

An embodiment of a rotation latch 2100 is shown in FIGS. 21A-C. In this embodiment, the latch 2100 includes a spring-loaded latch arm 2101 connected to a fixed latch portion 2102 by a pivot bearing 2103, as shown in FIG. 21A. The latch 2100 may be mounted to a first portion of the system that rotates (e.g., upper portion of the gimbal 30 and gantry 40, collectively the "rotating components") with respect to a second portion of the system (e.g., the base 20, the drive mechanism 70 and a lower portion of the gimbal 30 mounted to the drive mechanism 70, collectively the "non-rotating portion" 2104). Alternatively, the latch may be located on the rotating portion of the system and engages with a latch receiver (receptacle) on the non-rotating portion of the system.

FIG. 21B shows a side view of a gimbal 30 and a bottom view of the gimbal 30 viewed along line A-A. As shown in FIG. 21B, a circular member 2105 is located on non-rotating portion 2104 (e.g., the lower portion of the gimbal 30 or the drive mechanism 70) and contains latch receivers 2107 which are precisely located at pre-determined angular positions. Other configurations may be utilized. In this embodiment, the latch receivers 2107 (receptacles) are at three locations, corresponding to "in line" position of the gimbal 30 (e.g., for transport), and +/−90 degrees (i.e., scanning positions). The larch arm 2101 may be spring biased against the outer circumference of the circular member 2015, and the nose 2019 of the latch 2011 may glide over the outer circumference of the circular member 2015 (such as via bushings 2111 shown in FIG. 21A) as the rotating components (e.g., upper portion of gimbal 30 and the gantry 40) rotate with respect to the non-rotating portion 2104 of the system. When the latch nose 2019 reaches a latch receiver 2107, the latch nose 2019 is pushed into the receiver 2107, locking the rotational position of the rotating components relative to the non-rotating portion 2104 of the system. The latch receivers 2107 may be located at any arbitrary angular position around the circumference of the circular member 2105. The latch 2100 may be adjusted using adjustment screws to ensure that the rotating components are at the precise desired rotational angle relative to the non-rotating portion 2104 when the latch engages. For example, for an imaging scan, it may be important that the gimbal 30 and gantry 40 are precisely perpendicular to the long axis of the base 20 (e.g., the patient axis). The latch 2100 may be released via a cable 2113 that is attached to the latch arm 2101 and may extend through the interior of the gantry 30 (e.g., up through an arm 31 of the gantry 30) to a release mechanism (not visible in FIG. 21B). When the latch 2100 is released, the rotating components may rotate with respect to the non-rotating portion 2104 of the system.

In embodiments, the latch nose 2109 and receivers 2107 may have mating tapered faces to provide zero backlash. The two faces 2117a, 2117b of the tapered latch nose 2109 may be at different angles, as shown in FIG. 21C. For each latch nose face 2117a, the line of force to the latch pivot 2103 may be perpendicular to the latch nose face 2117a. The normal force of the nose may be inside the latch ring circle 2119 (defined by the circular member 2105 shown in FIG. 21B) so the latch 2100 will not "cam out" under load. This, the latch 2100 may hit exactly the right spot every time to maintain proper angle and alignment of the system, and the latch nose 2109 will not "cam out" of the receiver slot 2107, resulting in high reliability.

Embodiments may include a system having a cable management system. In embodiments, a first plurality of cables may extend between the sides of the gimbal 30, and a second plurality of cables may extend between the gimbal 30 and the base 20/drive mechanism 70. It may be challenging to manage the second plurality cables, particularly as the gimbal 30 rotates with respect to the base 20 and drive mechanism 70. A cable management system 2200 according to one embodiment is shown in FIGS. 22A-D and 23A-C. In various embodiments, a first plurality of cables may extend across the gimbal 30 and rotate with the gimbal 30 with respect to the base 20. A second plurality of cables may enter the gimbal via an opening that rotates and extend into a service loop that extends into an arm of the gimbal, and may rotate with the gimbal with respect to the base. Rotation of the gimbal in a first direction causes the cable to be pulled up into the gimbal arm, and rotation in a second direction may cause the cables to extend out of the loop. The first plurality of cables may be secured within the gimbal so as to avoid interference with the second group as the gimbal rotates.

Figure 22A:
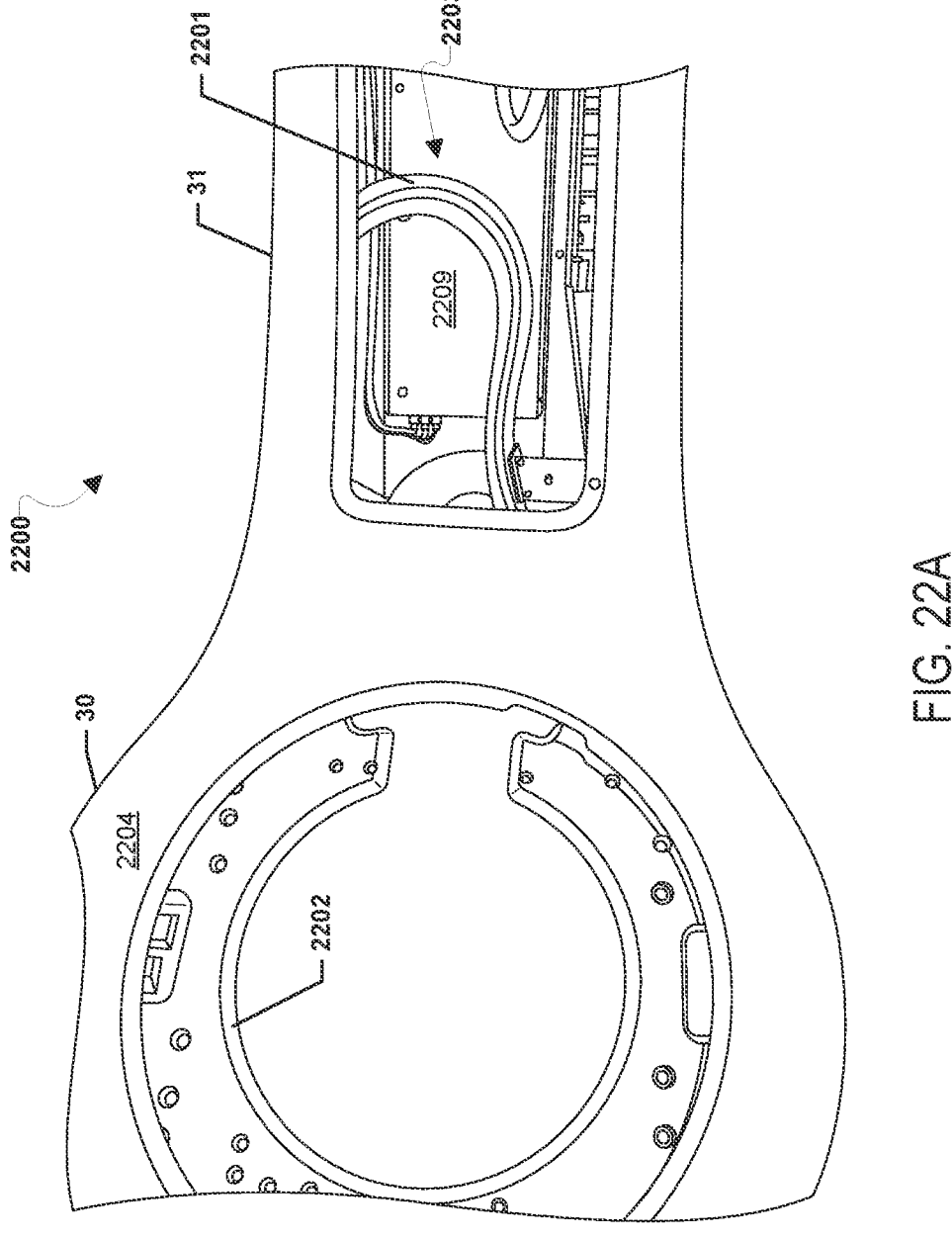
FIGS. 22A-D illustrate a cable management system according to one embodiment.

FIG. 22A is a top partial view of a gimbal 30 with the covers 205, 207 (see FIG. 2B) removed. The gimbal 30 may include a lower portion 2202 that may be fixed to the drive mechanism (e.g., fixed carriage) and may comprise part of the non-rotating portion of the system, as described above. An upper portion 2204 of the gimbal 30 may rotate with respect to the non-rotating portion of the system, such as via a bearing system between the upper 2204 and lower 2202 portions of the gimbal 30. The gantry 40 and imaging components may be attached to the upper portion 2204 of the gimbal 30 as described above. One or more cables 2201 connecting the non-rotating portion of the system to the rotating portion of the system (e.g., providing power and/or data between the portions) may be fed up from the drive mechanism 70 and/or base 20 through an opening in the gimbal 30 and may be fed up through a chute 2205 (see FIGS. 22B-D) into the interior of an arm 31 of the gimbal 30. The one or more cables 2201 may form a service loop 2203 within the arm 31 of the gantry 30, as shown in FIG. 22A. One end 2207 of the loop 2203 may be fixed to the upper (i.e., rotating) portion 2204 of the gantry 30 (see FIGS. 23A-C), and the opposite end of the loop may be free to feed in and out through the chute 2205 as the upper portion 2204 rotates. The arm 31 may include a generally flat interior surface 2209 to allow the service loop 2203 to slide up and down within the gimbal arm 31 as the cable(s) 2201 are fed into and out from the loop 2203.

Figure 22B:
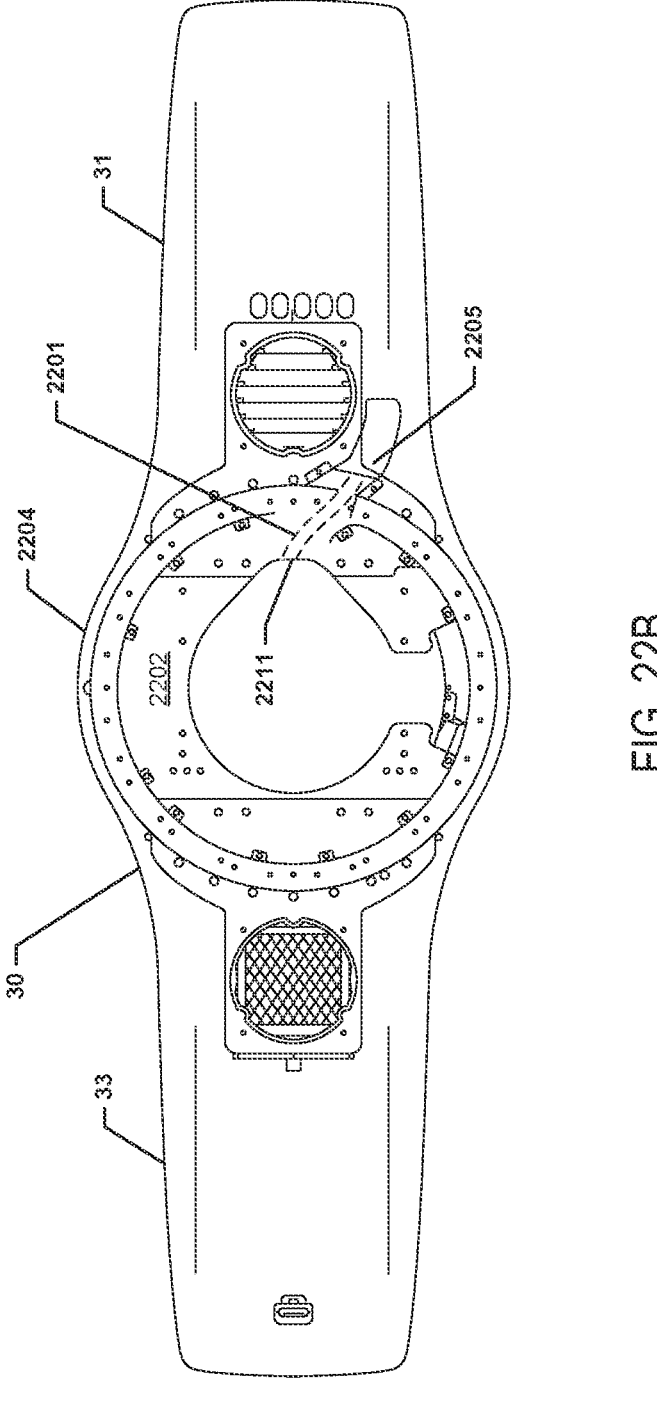
Figure 22C:
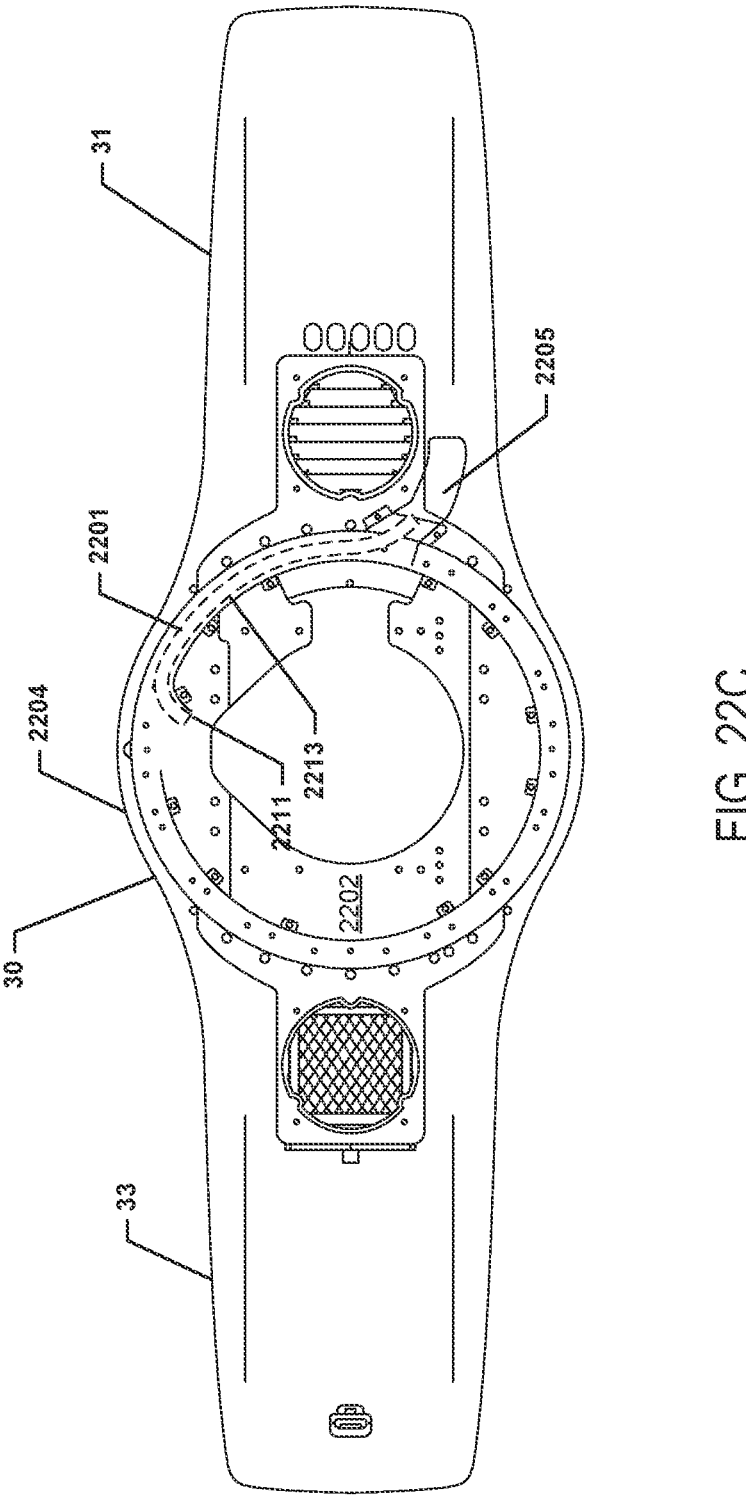
Figure 22D:
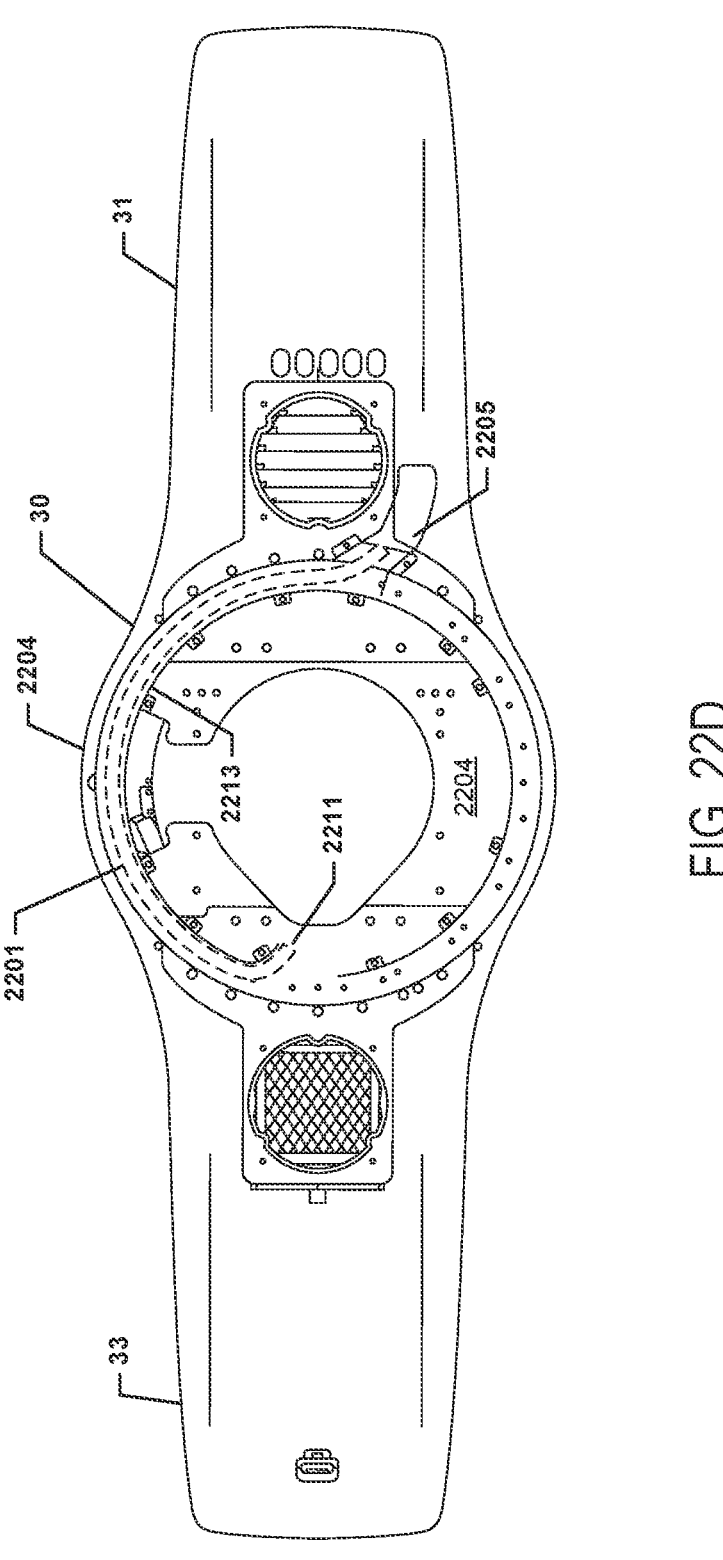

FIGS. 22B-D are bottom views of the gimbal 30 that schematically illustrate the one or more cables 2201 being fed into and out of the service loop in the gimbal arm 31 as the upper portion 2204 of the gimbal 30 rotates relative to the lower portion 2202. In FIG. 22B, the gimbal 30 may be in an "in-line" position relative to the base 20 (e.g., a transport position). The one or more cables 2201 may be fixed to the lower (i.e., non-rotating) portion 2202 of the gimbal 30 at a position 2211 that is proximate to the opening or chute 2205 that feeds the cables 2201 up into the service loop in the gimbal arm 31. In FIG. 22C, the upper portion 2204 of the gimbal 30 is rotated 90° from the "in-line" position of FIG. 22B, and may be oriented perpendicular to the base 20 (e.g., a scan position), such as shown in FIG. 1. The rotation of the upper portion 2204 relative to the lower portion 2202 causes the one or more cables 2201 to be fed out from the service loop as shown in FIG. 22C. Rotating the upper portion 2204 in the opposite direction (e.g., back to the position of FIG. 22B) causes the one or more cables 2201 to be fed back up through the opening/chute 2205 into the service loop. FIG. 22D shows the gimbal 30 rotated 180° relative to the position of FIG. 22B (i.e., back to an "in-line" configuration with the positions of the arms 31, 33 switched relative to FIG. 22B). In this position, the cables 2201 may be substantially completely fed out from the service loop.

The one or more cables 2201 may be located within a channel 2213 formed in the gimbal 30 as the cable(s) 2201 are fed out from the service loop. As shown in FIG. 22D, for example, the channel 2213 extends proximate to the outer circumference of the lower (i.e., non-rotating) portion 2202 of the gimbal 30 along one side of the gimbal 30. By confining the cables 2201 in channels 2213, they may be prevented from interfering with other components within the gimbal, such as separate cables running between the arms 31, 32 of the gimbal. Multiple channels 2213 may be provided (e.g., at different radial positions on the lower non-rotating portion 2202 of the gimbal). Each channel 2213 may contain a bundle of cables, which may be vertically stacked and enclosed in a protective covering, for example. Channels 2213 located closer to the outer circumference of the gimbal 30 may require a larger service loop 2203 in the gimbal arm 31 because the cables must travel a greater distance as the gimbal rotates.

Figures 23A, 23B, 23C:
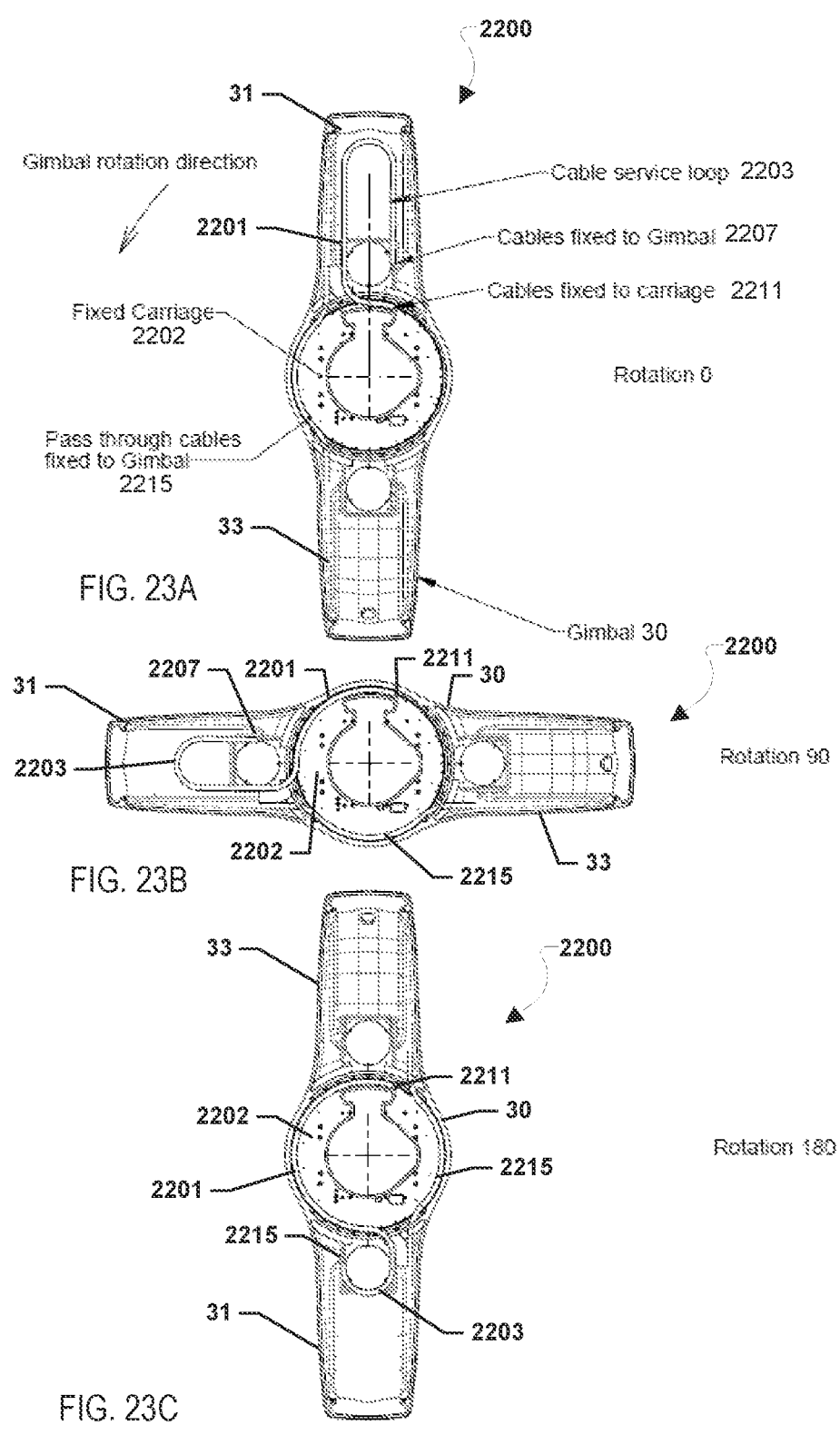
FIGS. 23A-C illustrate the location of the cables in a gimbal that is rotated by 0° (FIG. 23A), 90° (FIG. 23B) and 180° (FIG. 23C).

FIGS. 23A-23C are top views of the gimbal 30 schematically illustrating the cable management system 2000 according to one embodiment. In this view, a second group 2215 of one or more cables is shown extending between the respective arms 31, 33 of the gimbal 30. The second cable group 2215 may extend proximate to the outer circumference of the base of the gimbal 30 on the opposite side as the first group of one or more cables 2201 (i.e., on the opposite side of the gimbal rotation axis), so that the two cable groups do not interfere with each other. FIG. 23A shows the gimbal 30 at 0° rotation relative to the base (corresponding to the "in-line" position of FIG. 22B), FIG. 23B shows the gimbal at a 90° rotation (corresponding to the scanning position of FIG. 22C), and FIG. 23C shows the gimbal at a 180° rotation (corresponding to the "in-line" position of FIG. 22D). FIGS. 23A-C also illustrate the service loop 2203 increasing or decreasing in size depending on the rotational position of the gimbal 30.

Alternatively or in addition to the cables 2201 described above, in some embodiments at least a portion of the power and/or data may be passed between the rotating portion (gimbal, gantry, etc.) and the non-rotating portion (e.g., base, drive mechanism) of the system via a slip ring.

FIGS. 24A-E illustrate a gimbal 30 having a spherically shaped outer surface 2400 that faces the gantry 40 according to an embodiment. As described above, the gantry 40 may be attached to the gimbal 30 at two pivot points and may tilt with respect to the gimbal 30. During this tilt motion, the gantry 40 swings through an arc over the outer surface of the gimbal 30 facing the gantry 40. The gantry 40 may have relatively sharp corners which may interfere with the gantry 40 swinging over the surface of the gimbal 30 and may require the gantry 40 to be raised away from the surface of the gimbal 30 and thus higher from the ground to provide the necessary clearance. This may produce mechanical instability and increase the size of the system.

Figures 24A, 24B, 24C, 24D, 24E:
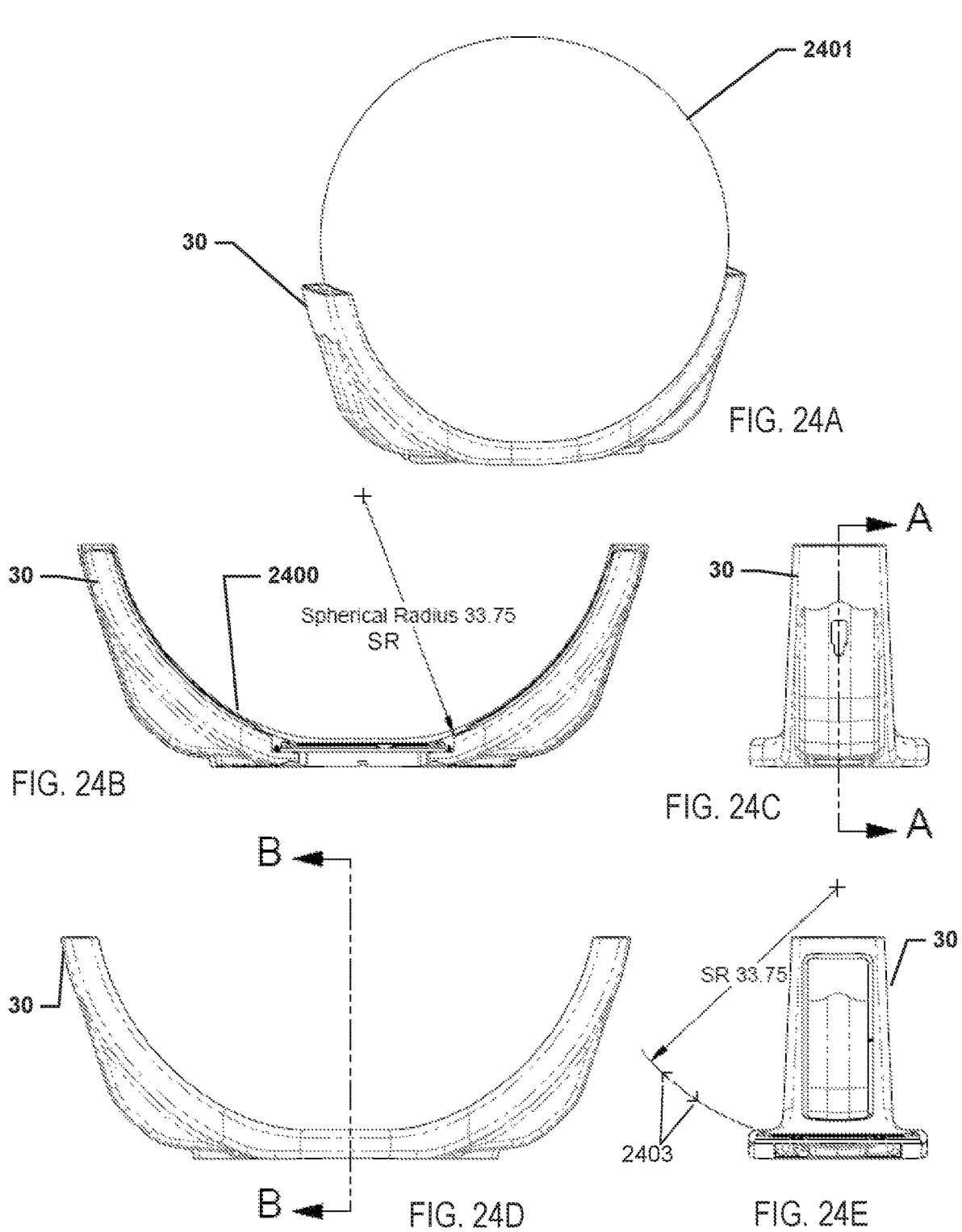
FIGS. 24A-E illustrate a gimbal having a generally spherical surface.

In one embodiment, the surface 2400 of the gimbal 30 which faces the gantry has a generally concave contour (e.g., curved, angled or both) along the direction through which the gantry 40 swings during tilt motion. In embodiments, the surface 2400 of the gimbal 30 may be substantially spherical, as illustrated schematically by the imaginary sphere 2401 contacting the surface 2400 of the gimbal 30 in FIG. 24A. The sphere 2401 may be considered an extension of the surface 2400 of the gimbal 30 that faces the gantry 40 (as shown, for instance, in FIG. 1). As shown in the side view of FIG. 24B, the surface 2400 of the gimbal 30 may have a circular cross-section with a radius, SR, in a direction transverse to the tilt direction of the gantry 40 (i.e., into and out of the page in FIG. 24B). The surface 2400 of the gimbal 30 may be generally concentric with the outer diameter of the O-shaped gantry ring 40 that is supported by the gimbal 30. In addition, the surface 2400 of the gimbal 30 may also have a circular cross-section along the tilt direction of the gantry (i.e., in the direction of arrows 2403 in FIG. 24E), as is shown in the side view of FIG. 24E. The radius of the circular-cross section of FIG. 24E may be the same radius (i.e., SR) as in FIG. 24B. Thus, the surface 2400 facing the gantry 40 may define a portion of a sphere 2401 as shown in FIG. 24A. This configuration may allow the gantry 40 to be mounted lower on the system, such that the gantry 40 may nest within the gimbal 30 with an extremely small clearance between the gimbal 30 and gantry 40, while still permitting the gantry 40 to freely tilt with respect to the gimbal 30. The configuration of FIGS. 24A-E may also provide added structural support for the gimbal 30.

Figures 25A, 25B, 25C:
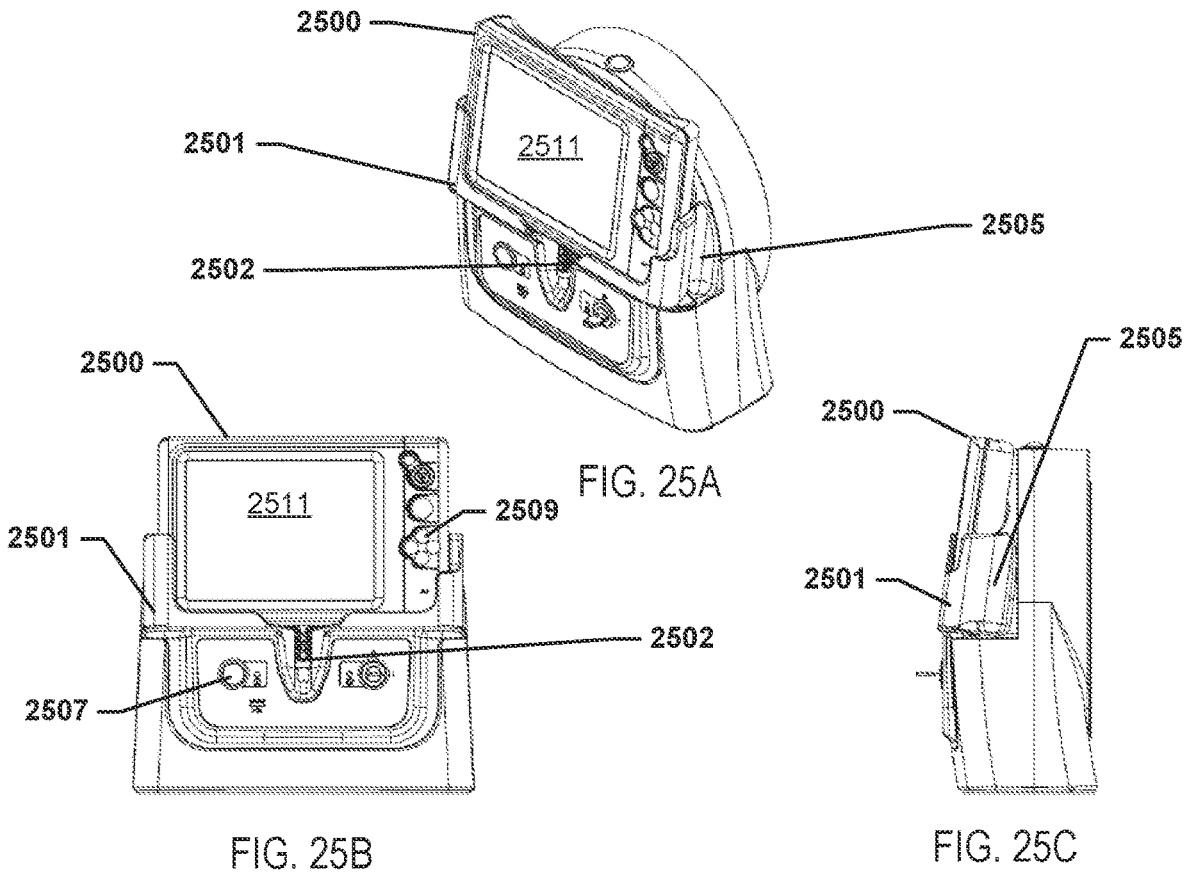
FIGS. 25A-C illustrate a user interface controller/display pendant in a holster according to one embodiment.

In embodiments, a mobile imaging system 100 such as described above may have a user interface (UI) device 2500, such as a touchscreen controller/display (e.g., 4-12 inch screen, such as a 7 inch screen), that may be removably mounted in a holster 2401 that is attached to the system 100 (e.g., on the gimbal 30, the gantry 40, or any other part of the system 100 that is easily accessible by a user), as shown in FIGS. 25A-C. The UI device 2500 may be used to control the system 100, and may receive and display feedback from the system. A cable 2502 may be attached to and/or plug into one of several ports on system to connect the user interface device 2500 to the system 100. The cable 2502 may be retractable into the system (e.g., within the gimbal 30) or may be located external to the system. The length of the cable 2502 may be 5-30 feet, such as 10-20 feet (e.g., 15 feet). For example, the UI device 2500 may be plugged into ports on either side of gimbal 30. This may enable a user holding the UI device 2500 to move around to any side of the system 100, step behind a lead barrier during x-ray imaging, etc., while operating the system 100 through a wired fashion, as may be required by applicable regulations. The UI device 2500 may also use a wireless interface with the system 100 where regulations allow.

FIGS. 25A-C show, respectively, perspective (FIG. 25A), front (FIG. 25B) and side (FIG. 25C) views of an embodiment user interface device 2500 mounted in a holster 2501. The holster 2501 may be located in any location on the system 100. In one preferred embodiment, the holster 2501 may be mounted to or integrally formed in a distal or "earmuff" portion 201, 203 of the gimbal 30, as described above in connection with FIG. 2B. The holster 2501 may have features 2505, such as grooves in the sides of the holster 2501, that may be gripped by a user to facilitate steering of the system 100 when the system is driven in transport mode. The holster 2501 may include one or more control inputs 2507 (e.g., buttons, switches, etc.) for the system 100. Additional control inputs (e.g., hard keys 2509) may be provided on the user interface device 2500. The user interface device 2500 may be a handheld device (e.g., a pendant device, a tablet device, etc.) that may be removed by sliding the device 2500 up and out of the holster 2501. The display 2511 may display system information and menu options that may enable a user to control the operation of the system. The user interface device 2500 may be operably connected to a control system of the device, such as the computer 46 in the gantry 40 shown in FIG. 3A, and/or one or more additional control units that may be located elsewhere on the device, such as in the gimbal 30, base 20, drive mechanism 70, etc. The user interface device 2500 may be used to control the operation of the system when it is both within the holster 2501 and removed from the holster 2501.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module executed which may reside on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A control system for an imaging device including a gantry having at least one imaging component and a gimbal supporting the gantry, comprising:
   a holster mounted to one of the gantry and the gimbal; and
   a user interface device removably received by the holster and operably connected to a control unit of the imaging device, the user interface device comprising a display configured to display system information and at least one user input component for controlling operation of the imaging device, wherein the holster limits movement of the user interface device in a plurality of degrees of freedom when the user interface device is received by the holster.

2. The control system of claim 1, wherein the user interface device comprises a handheld device that is operable to control the operation of the imaging device when the user interface device is located in the holster and when the user interface device is removed from the holster.

3. The control system of claim 1, wherein the user interface device is operably connected to the control unit of the imaging device by at least one of a wired and a wireless communication link.

4. The control system of claim 3, wherein the communication link has a range of up to about 30 feet from the imaging device.

5. The control system of claim 1, wherein the imaging device is a mobile imaging device, and the holster comprises at least one feature configured for steering of the imaging device during transport of the imaging device.

6. The control system of claim 1, wherein the imaging device further comprises a locking mechanism to prevent the gantry from translating relative to a base when the gantry is in a first angular position.

7. The control system of claim 6, wherein engaging the locking mechanism comprises translating the gantry relative to the base to a first translation position along a length dimension of the base.

8. The control system of claim 7, wherein the control unit is configured to control the position of the gantry relative to the base.

9. The control system of claim 1, wherein the imaging device includes a base, the gimbal connecting the gantry to the base.

10. The control system of claim 9, wherein the imaging device is a mobile imaging device, and the holster comprises at least one feature configured to control the movement of the imaging device.

11. The control system of claim 10, wherein the gantry is configured to move relative to the base, and the control unit is configured to control the position of the gantry relative to the base, such that the control unit controls the translation of the gantry relative to the base between a first translation position along a length dimension of the base and a second translation position.

12. The control system of claim 10, wherein the at least one feature of the holster is configured for steering of the imaging device during transport of the imaging device.

13. An imaging system, comprising:
   an imaging device including:
      a gantry having at least one imaging component;
      a gimbal that supports the gantry such that the gantry selectively tilts with respect to the gimbal in a gantry tilt direction;
      a base supporting the gimbal and the gantry, the base including a drive system; and
   a control system, the control system including:
      a user interface device operably connected to a control unit of the imaging device, the user interface device comprising a display configured to display system information and at least one user input component for controlling operation of the imaging device; and
      a holster located on one of the gantry and the gimbal, the holster configured to receive the user interface device to removably mount the user interface with the one of the gantry and the gimbal, wherein the holster limits movement of the user interface device in a plurality of degrees of freedom when the user interface device is received by the holster.

14. The imaging system of claim 13, wherein the user interface device comprises a handheld device that is operable to control the operation of the imaging device when the user interface device is located in the holster and when the user interface device is removed from the holster.

15. The imaging system of claim 13, wherein the user interface device is operably connected to the control unit of the imaging device by at least one of a wired and a wireless communication link.

16. The imaging system of claim 13, wherein the holster comprises at least one feature configured for steering of the imaging device during transport of the imaging device.

17. The imaging system of claim 13, wherein the gantry and gimbal are configured to translate along the base; and
   wherein the control unit is configured to control the position of the gantry relative to the base.

* * * * *